(12) United States Patent
Hoffman et al.

(10) Patent No.: US 9,637,738 B2
(45) Date of Patent: May 2, 2017

(54) METHODS AND AGENTS TO INCREASE THERAPEUTIC DYSTROPHIN EXPRESSION IN MUSCLE

(71) Applicants: Eric Hoffman, Kensington, MD (US); Alyson Fiorillo, Washington, DC (US)

(72) Inventors: Eric Hoffman, Kensington, MD (US); Alyson Fiorillo, Washington, DC (US)

(73) Assignee: Reveragen Biopharma, Inc., Rockville, MD (US)

(*) Notice: Subject to any disclaimer, the term of this patent is extended or adjusted under 35 U.S.C. 154(b) by 0 days.

(21) Appl. No.: 14/249,748

(22) Filed: Apr. 10, 2014

(65) Prior Publication Data

US 2014/0350069 A1 Nov. 27, 2014

Related U.S. Application Data

(60) Provisional application No. 61/810,483, filed on Apr. 10, 2013.

(51) Int. Cl.
| | | |
|---|---|---|
| C12N 15/11 | (2006.01) | |
| C12N 15/113 | (2010.01) | |
| A61K 31/573 | (2006.01) | |
| A61K 31/7088 | (2006.01) | |
| A61K 45/06 | (2006.01) | |

(52) U.S. Cl.
CPC .......... *C12N 15/113* (2013.01); *A61K 31/573* (2013.01); *A61K 31/7088* (2013.01); *A61K 45/06* (2013.01); *C12N 15/111* (2013.01); *C12N 2310/113* (2013.01); *C12N 2310/141* (2013.01); *C12N 2320/30* (2013.01)

(58) Field of Classification Search
None
See application file for complete search history.

(56) References Cited

U.S. PATENT DOCUMENTS

| 7,887,793 B2 | 2/2011 | Tremblay et al. |
| 2012/0040052 A1 | 2/2012 | Carrigan et al. |
| 2012/0129920 A1 | 5/2012 | Bozzoni et al. |

FOREIGN PATENT DOCUMENTS

| WO | WO 2011103573 A2 * | 8/2011 |
| WO | WO 2011127048 A2 * | 10/2011 |
| WO | 2012172012 | 12/2012 |

OTHER PUBLICATIONS

Kuang et al, Cyclic stretch induced miR-146a upregulation delays C2C12 myogenic differentiation through inhibition of Numb, 2009, Biochemical and Biophysical Research Communications, 378: 259-263.*

Gonzalez-Ramirez et al, Nuclear and Nuclear Envelope Localization of Dystrophin Dp71 and Dystrophin-Associated Proteins (DAPs) in the C2C12 Muscle Cells: DAPs Nuclear Localization Is Modulated During Myogenesis, 2008, Journal of Cellular Biochemistry, 105: 735-745.*
Hoffman et al, Restoring Dystrophin Expression in Duchenne Muscular Dystrophy Muscle, 2011, The American Journal of Pathology, vol. 179, 1: 12-22.*
GenBank entry M18533.1, 2000, *Homo sapiens* dystrophin mRNA, pp. 1-6.*
Cacchiarelli, et al., "miR-31 Modulates Dystrophin Expression: New Implications for Duchenne Muscular Dystrophy Therapy", EMBO Reports, Epub., vol. 12, No. 2, Jan. 7, 2011, pp. 136-141.
International Search Report and Written Opinion, PCT Application No. PCT/US2014/033656 dated Sep. 9, 2014, 11 pgs.
Muntoni, et al., "Targeting RNA to Treat Neuromuscular Disease", Nature Reviews Drug Discovery, vol. 10, No. 8, Aug. 1, 2001, pp. 621-637.
Anthony K, Arechavala-Gomeza V, Ricotti V, Torelli S, Feng L, Janghra N, Tasca G, Guglieri M, Barresi R, Armaroli A et al, Biochemical Characterization of Patients With In-Frame or Out-of-Frame DMD Deletions Pertinent to Exon 44 or 45 Skipping. JAMA Neurol, 2013, vol. 71, No. 1, pp. 32-40.
Anthony K, Cirak S, Torelli S, Tasca G, Feng L, Arechavala-Gomeza V, Armaroli A, Guglieri M, Straathof CS, Verschuuren JJ et al, Dystrophin quantification and clinical correlations in Becker muscular dystrophy: implications for clinical trials. Brain, 2011, 134: 3547-3559.
Beggs AH, Hoffman EP, Snyder JR, Arahata K, Specht L, Shapiro F, Angelini C, Sugita H, Kunkel LM, Exploring the molecular basis for variability among patients with Becker muscular dystrophy: dystrophin gene and protein studies. Am J Hum Genet, 1991, 49: 54-67.
Brown KJ, Marathi R, Fiorillo AA, Ciccimaro EF, Sharma S, Rowlands DS, Rayavarapu S, Nagaraju K, Hoffman EP, Hathout Y Accurate Quantitation of Dystrophin Protein in Human Skeletal Muscle Using Mass Spectrometry. J Bioanal Biomed Suppl 7, 2013, pp. 1-16.
Cacchiarelli D, Incitti T, Martone J, Cesana M, Cazzella V, Santini T, Sthandier O, Bozzoni I, miR-31 modulates dystrophin expression: new implications for Duchenne muscular dystrophy therapy. EMBO Rep., 2011, vol. 12, No. 2, pp. 136-141.
Cacchiarelli D, Martone J, Girardi E, Cesana M, Incitti T, Morlando M, Nicoletti C, Santini T, Sthandier O, Barberi L et al, MicroRNAs involved in molecular circuitries relevant for the Duchenne muscular dystrophy pathogenesis are controlled by the dystrophin/nNOS pathway. Cell Metab, Oct. 6, 2010, 12: 341-351.

(Continued)

*Primary Examiner* — Kate Poliakova-Georgantas
(74) *Attorney, Agent, or Firm* — Dennis A. Bennett

(57) ABSTRACT

Agents and methods for increasing dystrophin protein expression in muscle through blocking of specific microRNAs and microRNA binding sites on the dystrophin 3' untranslated region (miR-146a, miRNA-146b, miR-223, miR-320a, miR374a, and miR-382). Methods for increasing the amount of dystrophin useful for effective therapeutic intervention for Becker muscular dystrophy, Duchenne muscular dystrophy, and other disorders where loss of dystrophin from muscle causes pathology.

8 Claims, 16 Drawing Sheets

(56) References Cited

OTHER PUBLICATIONS

Chamberlain JS, Grant SG, Reeves AA, Mullins LJ, Stephenson DA, Hoffman EP, Monaco AP, Kunkel LM, Caskey CT, Chapman VM, Regional localization of the murine Duchenne muscular dystrophy gene on the mouse X chromosome. Somat Cell Mol Genet, 1987, vol. 13, No. 6, pp. 671-678.

Chen JF, et al., The role of microRNA-1 and microRNA-133 in skeletal muscle proliferation and differentiation. Nat Genet, Feb. 2006, vol. 38, No. 2, pp. 228-233.

Cirak S, Arechavala-Gomeza V, Guglieri M, Feng L, Torelli S, Anthony K, Abbs S, Garralda ME, Bourke J, Wells DJ et al, Exon skipping and dystrophin restoration in patients with Duchenne muscular dystrophy after systemic phosphorodiamidate morpholino oligomer treatment: an open-label, phase 2, dose-escalation study. Lancet, Aug. 13, 2001, vol. 378, pp. 595-605.

Eisenberg I, Eran A, Nishino I, Moggio M, Lamperti C, Amato AA, Lidov HG, Kang PB, North KN, Mitrani-Rosenbaum S et al, Distinctive patterns of microRNA expression in primary muscular disorders. Proc Natl Acad Sci U S A, Jan. 8, 2008, vol. 1505, No. 1, pp. 17016-17021.

Finkel RS, Flanigan KM, Wong B, Bonnemann C, Sampson J, Sweeney HL, Reha A, Northcutt VJ, Elfring G, Barth J et al, Phase 2a study of ataluren-mediated dystrophin production in patients with nonsense mutation duchenne muscular dystrophy. PLoS One, Dec. 2013, vol. 8, Issue 12, pp. 1-11.

Greco S, et al., Common micro-RNA signature in skeletal muscle damage and regeneration induced by Duchenne muscular dystrophy and acute ischemia. Cell Metab, Oct. 2009, vol. 23, pp. 341-351.

Heier CR, Damsker JM, Yu Q, Dillingham BC, Huynh T, Van der Meulen JH, Sali A, Miller BK, Phadke A, Scheffer L et al (2013) VBP15, a novel anti-inflammatory and membrane-stabilizer, improves muscular dystrophy without side effects. EMBO Mol Med, 2013, 5: 1569-1585.

Hoffman EP, Bronson A, Levin AA, Takeda S, Yokota T, Baudy AR, Connor EM (2011) Restoring dystrophin expression in duchenne muscular dystrophy muscle progress in exon skipping and stop codon read through. Am J Pathol, Jul. 2011, vol. 179, No. 1, pp. 12-22.

Hoffman EP, Brown RH, Jr., Kunkel LM, Dystrophin: the protein product of the Duchenne muscular dystrophy locus, 1987, Cell 51: 919-928.

Hoffman EP, Fischbeck KH, Brown RH, Johnson M, Medori R, Loike JD, Harris JB, Waterston R, Brooke M, Specht L et al, Characterization of dystrophin in muscle-biopsy specimens from patients with Duchenne's or Becker's muscular dystrophy. N Engl J Med, 1988, 318: 1363-1368.

Hoffman EP, Kunkel LM, Angelini C, Clarke A, Johnson M, Harris JB, Improved diagnosis of Becker muscular dystrophy by dystrophin testing. Neurology, 1989, 39: 1011-1017.

Hoffman EP, Monaco AP, Feener CC, Kunkel LM, Conservation of the Duchenne muscular dystrophy gene in mice and humans. Science, Oct. 16, 1987, 238: 347-350.

Hoshino S, Ohkoshi N, Ishii A, Shoji S, The expression of dystrophin, alpha-sarcoglycan, and beta-dystroglycan during skeletal muscle regeneration: immunohistochemical and western blot studies. Acta Histochem, 2002, 104: 139-147.

Huynh T, Uaesoontrachoon K, Quinn JL, Tatem KS, Heier CR, Van Der Meulen JH, Yu Q, Harris M, Nolan CJ, Haegeman G et al, Selective modulation through the glucocorticoid receptor ameliorates muscle pathology in mdx mice. J Pathol, 2013, 231: 223-235.

Kesari A, Pirra LN, Bremadesam L, McIntyre O, Gordon E, Dubrovsky AL, Viswanathan V, Hoffman EP, Integrated DNA, cDNA, and protein studies in Becker muscular dystrophy show high exception to the reading frame rule. Hum Mutat, 2008, 29: 728-737.

Livak KJ, Schmittgen TD, Analysis of relative gene expression data using real-time quantitative PCR and the 2(-Delta Delta C(T)) Method. Methods, 2001, 25: 402-408.

Lu QL, Morris GE, Wilton SD, Ly T, Artem'yeva OV, Strong P, Partridge TA, Massive idiosyncratic exon skipping corrects the nonsense mutation in dystrophic mouse muscle and produces functional revertant fibers by clonal expansion. J Cell Biol, Mar. 6, 2000, vol. 148, No. 5, pp. 985-996.

Mamchaoui K, Trollet C, Bigot A, Negroni E, Chaouch S, Wolff A, Kandalla PK, Marie S, Di Santo J, St Guily JL et al, Immortalized pathological human myoblasts: towards a universal tool for the study of neuromuscular disorders. Skelet Muscle, 2011, 1: 34.

Mendell J, Rodino-Klapac LR, Sahenk Z, Roush K, Bird L, Lowes LP, Alfano L, Gomez AM, Lewis S, Kota J et al, Eteplirsen for the treatment of Duchenne muscular dystrophy. Ann Neurol, 2013, vol. 74, No. 5, pp. 637-647.

Naguibneva I, et al., The microRNA miR-181 targets the homeobox protein HOX-A11 during mammalian myoblast differentiation. Nat Cell Biol, Mar. 2006, vol. 8, No. 3, pp. 278-284.

Nghiem PP, Hoffman EP, Mittal P, Brown KJ, Schatzberg SJ, Ghimbovschi S, Wang Z, Kornegay JN Sparing of the dystrophin-deficient cranial sartorius muscle is associated with classical and novel hypertrophy pathways in GRMD dogs. Am J Pathol, Nov. 2013, 183: 1411-1424.

Roberts TC, et al Expression analysis in multiple muscle groups and serum reveals complexity in the microRNA transcriptome of the mdx mouse with implications for therapy. Mol Ther Nucleic Acids, 2012, 1:e39.

Schmittgen TD, Real-time quantitative PCR. Methods, 2001, 25: 383-385.

Spitali P, van den Bergen JC, Verhaart IE, Wokke B, Janson AA, van den Eijnde R, den Dunnen JT, Laros JF, Verschuuren JJ, t Hoen PA et al, DMD transcript imbalance determines dystrophin levels. FASEB J, Dec. 2013, vol. 27, pp. 4909-4916.

Sylvius N, et al. MicroRNA expression profiling in patients with lamin A/C-associated muscular dystrophy. FASED J, Nov. 2011, vol. 25, pp. 3966-3978.

Townsend D, Daly M, Chamberlain JS, Metzger JM, Age-dependent dystrophin loss and genetic reconstitution establish a molecular link between dystrophin and heart performance during aging. Mol Ther, Oct. 2011, vol. 19, No. 10, pp. 1821-1825.

van den Bergen JC, Wokke BH, Janson AA, van Duinen SG, Hulsker MA, Ginjaar HB, van Deutekom JC, Aartsma-Rus A, Kan HE, Verschuuren JJ, Dystrophin levels and clinical severity in Becker muscular dystrophy patients. J Neurol Neurosurg Psychiatry, 2014, vol. 85, pp. 747-753.

van Rooij E, Marshall WS, Olson EN, Toward microRNA-based therapeutics for heart disease: the sense in antisense. Circ Res, Oct. 24, 2008, 103: 919-928.

van Rooij E, Sutherland LB, Thatcher JE, DiMaio JM, Naseem RH, Marshall WS, Hill JA, Olson EN Dysregulation of microRNAs after myocardial infarction reveals a role of miR-29 in cardiac fibrosis. Proc Natl Acad Sci U S A, Sep. 2, 2008, vol. 105, No. 35, pp. 13027-13032.

Vignier N, Amor F, Fogel P, Divallet A, Poupiot J, Charrier S, Arock M, Montus M, Nelson I, Richard I et al, Distinctive serum miRNA profile in mouse models of striated muscular pathologies. PLoS One, Feb. 2013, vol. 8, Issue 2: e55281, pp. 1-14.

Wu B, Lu P, Cloer C, Shaban M, Grewal S, Milazi S, Shah SN, Moulton HM, Lu QL, Long-term rescue of dystrophin expression and improvement in muscle pathology and function in dystrophic mdx mice by peptide-conjugated morpholino. Am J Pathol, Aug. 2012, vol. 181, No. 2, pp. 392-400.

Yokota T, Lu QL, Partridge T, Kobayashi M, Nakamura A, Takeda S, Hoffman E, Efficacy of systemic morpholino exon-skipping in Duchenne dystrophy dogs. Ann Neurol, Jun. 2009, 65: 667-676.

Yokota T, Nakamura A, Nagata T, Saito T, Kobayashi M, Aoki Y, Echigoya Y, Partridge T, Hoffman EP, Takeda S, Extensive and prolonged restoration of dystrophin expression with vivo-morpholino-mediated multiple exon skipping in dystrophic dogs. Nucleic Acid Ther, Nov. 5, 2012, vol. 22, pp. 306-315.

Zhang X, Azhar G, Wei JY, The expression of microRNA and microRNA clusters in the aging heart. PLoS One, Apr. 2012, vol. 7, No. 4, e34688, pp. 1-13.

\* cited by examiner

SEQUENCE LISTING

<160> NUMBER OF SEQ ID NOS: 33

<210> SEQ ID NO 1
<211> LENGTH: 22
<212> TYPE: RNA
<213> ORGANISM: Homo sapiens

<400> SEQUENCE: 1
uuggguaccu uaagucaaga gu                                              22

<210> SEQ ID NO 2
<211> LENGTH: 22

```
<212> TYPE: RNA
<213> ORGANISM: Homo sapiens

<400> SEQUENCE: 2
uuggguaccu uaagucaaga gu                                              22

<210> SEQ ID NO 3
<211> LENGTH: 22
<212> TYPE: RNA
<213> ORGANISM: Homo sapiens

<400> SEQUENCE: 3
ucggauaccu uaagucaaga gu                                              22

<210> SEQ ID NO 4
<211> LENGTH: 22
<212> TYPE: RNA
<213> ORGANISM: Homo sapiens

<400> SEQUENCE: 4
ucggauaccu uaagucaaga gu                                              22

<210> SEQ ID NO 5
<211> LENGTH: 22
<212> TYPE: RNA
<213> ORGANISM: Homo sapiens

<400> SEQUENCE: 5
accccauaaa cuguuugacu gu                                              22

<210> SEQ ID NO 6
<211> LENGTH: 22
<212> TYPE: RNA
<213> ORGANISM: Homo sapiens

<400> SEQUENCE: 6
accccauaaa cuguuugacu gu                                              22

<210> SEQ ID NO 7
<211> LENGTH: 22
<212> TYPE: RNA
<213> ORGANISM: Homo sapiens

<400> SEQUENCE: 7
agcgggagag uugggucgaa aa                                              22

<210> SEQ ID NO 8
<211> LENGTH: 22
<212> TYPE: RNA
<213> ORGANISM: Homo sapiens

<400> SEQUENCE: 8
agcgggagag uugggucgaa aa                                              22

<210> SEQ ID NO 9
<211> LENGTH: 22
<212> TYPE: RNA
<213> ORGANISM: Homo sapiens

<400> SEQUENCE: 9
gugaauaguc caacauaaua uu                                              22
```

```
<210> SEQ ID NO 10
<211> LENGTH: 22
<212> TYPE: RNA
<213> ORGANISM: Mus musculus

<400> SEQUENCE: 10
gugaaucguc caacauaaua ua                                             22

<210> SEQ ID NO 11
<211> LENGTH: 22
<212> TYPE: RNA
<213> ORGANISM: Homo sapiens

<400> SEQUENCE: 11
gugaauaguc caacauaaua uu                                             22

<210> SEQ ID NO 12
<211> LENGTH: 22
<212> TYPE: RNA
<213> ORGANISM: Homo sapiens

<400> SEQUENCE: 12
gugaauaguc caacauaaua uu                                             22

<210> SEQ ID NO 13
<211> LENGTH: 22
<212> TYPE: RNA
<213> ORGANISM: Homo sapiens

<400> SEQUENCE: 13
gugaauaguc caacauaaua uu                                             22

<210> SEQ ID NO 14
<211> LENGTH: 22
<212> TYPE: RNA
<213> ORGANISM: Homo sapiens

<400> SEQUENCE: 14
gcuuaggugg ugcuuguuga ag                                             22

<210> SEQ ID NO 15
<211> LENGTH: 22
<212> TYPE: RNA
<213> ORGANISM: Homo sapiens

<400> SEQUENCE: 15
gcuuaggugg ugcuuguuga ag                                             22

<210> SEQ ID NO 16
<211> LENGTH: 47
<212> TYPE: RNA
<213> ORGANISM: Homo sapiens

<400> SEQUENCE: 16
ugauuguuca uaauacauaa aguucucugu aauuacaacu aaauuau                  47

<210> SEQ ID NO 17
<211> LENGTH: 47
<212> TYPE: RNA
<213> ORGANISM: Homo sapiens
```

-continued

<400> SEQUENCE: 17
augauuguuc auaauacaua aaguucucug uaauuacaac uaaauua         47

<210> SEQ ID NO 18
<211> LENGTH: 37
<212> TYPE: RNA
<213> ORGANISM: Homo sapiens

<400> SEQUENCE: 18
aaguauauaa auacuauagu uauauagaua aagagau                   37

<210> SEQ ID NO 19
<211> LENGTH: 34
<212> TYPE: RNA
<213> ORGANISM: Homo sapiens

<400> SEQUENCE: 19
cagguacuga guucuuacuu gaguaucaua auau                      34

<210> SEQ ID NO 20
<211> LENGTH: 33
<212> TYPE: RNA
<213> ORGANISM: Homo sapiens

<400> SEQUENCE: 20
uuugugaagg guagugguau uauacuguag auu                       33

<210> SEQ ID NO 21
<211> LENGTH: 27
<212> TYPE: RNA
<213> ORGANISM: Homo sapiens

<400> SEQUENCE: 21
aauacacagg acuuauuaua ucagagu                              27

<210> SEQ ID NO 22
<211> LENGTH: 37
<212> TYPE: RNA
<213> ORGANISM: Homo sapiens

<400> SEQUENCE: 22
ccaaauauau gccuuacuau uguauuauag uacugcu                   37

<210> SEQ ID NO 23
<211> LENGTH: 47
<212> TYPE: RNA
<213> ORGANISM: Homo sapiens

<400> SEQUENCE: 23
agcuccagau guuucucauu uuaaacaacu uuccacugac aacgaaa         47

<210> SEQ ID NO 24
<211> LENGTH: 25
<212> TYPE: DNA
<213> ORGANISM: Homo sapiens

<400> SEQUENCE: 24
acagagaact ttatgtatta tgaac                                25

<210> SEQ ID NO 25
<211> LENGTH: 25
<212> TYPE: DNA

```
<213> ORGANISM: Homo sapiens

<400> SEQUENCE: 25
acagagaact ttatgtatta tgaac                                              25

<210> SEQ ID NO 26
<211> LENGTH: 25
<212> TYPE: DNA
<213> ORGANISM: Homo sapiens

<400> SEQUENCE: 26
atgatactca agtaagaact cagta                                              25

<210> SEQ ID NO 27
<211> LENGTH: 25
<212> TYPE: DNA
<213> ORGANISM: Homo sapiens

<400> SEQUENCE: 27
acagtataat accactaccc ttcac                                              25

<210> SEQ ID NO 28
<211> LENGTH: 25
<212> TYPE: DNA
<213> ORGANISM: Homo sapiens

<400> SEQUENCE: 28
ctgatataat aagtcctgtg tattc                                              25

<210> SEQ ID NO 29
<211> LENGTH: 25
<212> TYPE: DNA
<213> ORGANISM: Homo sapiens

<400> SEQUENCE: 29
cagtactata atacaatagt aaggc                                              25

<210> SEQ ID NO 30
<211> LENGTH: 25
<212> TYPE: DNA
<213> ORGANISM: Homo sapiens

<400> SEQUENCE: 30
cgttgtcagt ggaaagttgt ttaaa                                              25

<210> SEQ ID NO 31
<211> LENGTH: 11
<212> TYPE: RNA
<213> ORGANISM: Homo sapiens

<400> SEQUENCE: 31
uaagucaaga g                                                             11

<210> SEQ ID NO 32
<211> LENGTH: 11
<212> TYPE: RNA
<213> ORGANISM: Homo sapiens

<400> SEQUENCE: 32
auucaguucu c                                                             11
```

```
<210> SEQ ID NO 33
<211> LENGTH: 25
<212> TYPE: DNA
<213> ORGANISM: Mus musculus

<400> SEQUENCE: 33
ggccaaacct cggcttacct gaaat                                      25
```

METHODS AND AGENTS TO INCREASE THERAPEUTIC DYSTROPHIN EXPRESSION IN MUSCLE

This application claims the benefit of priority of U.S. provisional application No. 61/810,483, filed Apr. 10, 2013, the disclosure of which is hereby incorporated by reference as if written herein in its entirety.

Disclosed herein are methods and agents that increase dystrophin protein expression in muscle through blocking of specific microRNAs and microRNA binding sites on the dystrophin 3' untranslated region (miR-146a, miR-146b, miR-223, miR-320a, miR-374, and miR-382). Further disclosed are methods to increase the amount of dystrophin useful for effective therapeutic intervention for Becker muscular dystrophy, Duchenne muscular dystrophy, and other disorders where loss of dystrophin from muscle causes pathology.

BACKGROUND

A microRNA ("miRNA") is a small, about 22 nucleotide long non-coding RNA molecule encoded by eukaryotic nuclear DNA. MicroRNA regulates gene expression transcriptionally and post-transcriptionally by base pairing with partially or fully complementary mRNA sequences which can result in translational repression of the mRNA and gene silencing or mRNA target degradation.

Duchenne muscular dystrophy is caused by loss of function mutations of the X-linked DMD gene, leading to lack of dystrophin protein at the muscle myofiber plasma membrane (Chamberlain et al., 1987; Hoffman et al., 1987a; Hoffman et al., 1988; Hoffman et al., 1987b). Becker muscular dystrophy is caused by present but abnormal dystrophin, in quality (molecular weight), or quantity (reduced percentage relative to normal muscle), or both (Beggs et al., 1991; Hoffman et al., 1989; Kesari et al., 2008). The relative amount of dystrophin protein in Becker patient muscle varies greatly, within a single muscle fiber ('patchy' immunostaining on subsections of myofiber membrane), between muscle fibers, and between patients. The amount of dystrophin only partially correlates with phenotype (<10% normal levels often more severe phenotypes; >10% moderate, mild, or asymptomatic phenotypes) (Hoffman et al., 1989; van den Bergen et al., 2013). The molecular underpinning for variable quantities of dystrophin include variable protein stability, variable mRNA stability, and variable mRNA translation. There is limited evidence for variable mRNA stability correlated with variable dystrophin levels (Spitali et al., 2013) as well as location of mutation and effect on expression and stability of the resulting abnormal protein (Anthony et al., 2013; Anthony et al., 2014; Anthony et al., 2011). However, series of patients with the same in-frame deletion of exons 45-47 show quite variable levels of dystrophin in their muscle, ranging from 5%-80% normal levels (Hoffman et al., 2011; Kesari et al., 2008). Patients with the same common in-frame exon 45-47 deletion mutation would be expected to show similar gene expression, similar mRNA stability, and the same mutant protein (same deleted amino acids) with expected similar stability. Thus, the molecular causes for the variable dystrophin levels in Becker patients with exon 45-47 deletions, and likely all Becker patients, have remained elusive.

Understanding the regulation of dystrophin protein quantity and stability in patient muscle is required to monitor the success of dystrophin-rescue strategies currently under development for Duchenne muscular dystrophy. Two clinical programs aimed at dystrophin rescue, stop codon read through and exon skipping antisense, have shown quite variable success, both within a specific biopsy, and between patients (Cirak et al., 2011; Finkel et al., 2013; Mendell et al., 2013). The variability was particularly evident in high dose antisense mediated exon skipping in the dystrophin-deficient dog model of DMD, where many different muscles could be systematically sampled from the same treated dog (Yokota et al., 2009; Yokota et al., 2012). The small muscle biopsy obtained from each treated patient introduces a sampling error that may not be representative of the entire patient. However, the observed variability in dystrophin expression results in challenges in interpreting success of the treatments. Perhaps more importantly, understanding the molecular basis for variable dystrophin protein expression could lead to new interventions able to improve the reliability and success of dystrophin rescue therapies.

We hypothesize that the molecular mechanisms causing variable dystrophin protein levels in Becker muscular dystrophy patients harboring the same exon 45-47 deletion might also underlie the observed variable response of muscles to exon skipping therapy. As all patients with the same exon 45-47 in-frame deletion should all share the same type of dystrophin protein, protein stability or function should not be variables in driving dystrophin protein levels. We have found that dystrophin protein levels varied between 10 unrelated BMD patients sharing the same exon 45-47 in-frame deletion, yet mRNA levels were quite similar (and similar to normal volunteer muscle). However, microRNAs targeting the dystrophin mRNA showed a high degree of variability from biopsy to biopsy, and the levels and numbers of these microRNAs correlated well with dystrophin protein levels. Our data suggests that variable expression of microRNAs in patient muscle may drive observed variability in dystrophin protein levels in both BMD patients, and DMD patients treated with exon-skipping antisense therapy.

As described herein, the inventors identified the cause of variable dystrophin levels to be binding of specific microRNAs to the dystrophin mRNA 3' untranslated region (3' UTR). This enables new methods for treating dystrophin-related conditions, disorders, or diseases, such as Becker muscular dystrophy, by inhibiting these kinds of miRNAs to increase expression of dystrophin protein in cells, especially in patient muscle cells. The blocking of the specific microRNAs which inhibit dystrophin expression increases the translation of mRNA encoding dystrophin protein.

Novel compounds and pharmaceutical compositions, certain of which have been found to modulate dystrophin expression have been discovered, together with methods of synthesizing and using the compounds including methods for the treatment of dystrophin-mediated diseases in a patient by administering the compounds.

In certain embodiments of the present invention disclosed herein is a nucleic acid molecule or derivative thereof that binds to at least one of miR-146a, miR-146b-5p, miR-223, miR-320a, miR-374a, or miR-382 or to portions thereof, and that increases expression of dystrophin protein.

Certain compounds disclosed herein may possess useful dystrophin modulating activity, and may be used in the treatment or prophylaxis of a disease or condition in which dystrophin plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for modulating dystrophin. Other embodiments provide methods for treating a dystrophin-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the modulation dystrophin.

In certain embodiments of the present invention disclosed herein is a nucleic acid molecule or derivative that is partially complementary to at least one of miR-146a, miR-146b-5p, miR-223, miR-320a, miR-374a, or miR-382.

In certain embodiments of the present invention disclosed herein is a nucleic acid molecule or derivative that binds to the seed sequence of at least one of miR-146a, miR-146b-5p, miR-223, miR-320a, miR-374a, or miR-382, wherein said seed sequence binds to the 3'UTR of dsytrophin mRNA.

In certain embodiments of the present invention disclosed herein is a nucleic acid molecule or derivative that comprises a sequence that is fully complementary to the seed sequence of at least one of miR-146a, miR-146b-5p, miR-223, miR-320a, miR-374a, or miR-382.

In certain embodiments of the present invention disclosed herein is a nucleic acid molecule or derivative that comprises a sequence that is at least 70%, 75%, 80%, 85%, 90%, or 95% identical to a full complement of a seed sequence of at least one of miR-146a, miR-146b-5p, miR-223, miR-320a, miR-374a, or miR-382.

In certain embodiments of the present invention disclosed herein is a nucleic acid molecule or derivative that comprises a sequence that is fully complementary to at least one of miR-146a, miR-146b-5p, miR-223, miR-320a, miR-374a, or miR-382.

In certain embodiments of the present invention disclosed herein is a nucleic acid molecule or derivative that comprises a sequence that is at least 70%, 75%, 80%, 85%, 90%, or 95% identical to a full complement of at least one of miR-146a, miR-146b-5p, miR-223, miR-320a, miR-374a, or miR-382.

In certain embodiments of the present invention disclosed herein is a nucleic acid molecule or derivative that comprises a sequence that is fully complementary to the sequence of at least one of miR-146a, miR-146b-5p, miR-223, miR-320a, miR-374a, or miR-382, except it contains 1, 2, 3, 4, 5, 6, or 7 deletions, substitutions, or insertions to said fully complementary sequence.

In certain embodiments of the present invention disclosed herein is a nucleic acid molecule or derivative that comprises polynucleotide sequences complementary to at least two of miR-146a, miR-146b-5p, miR-223, miR-320a, miR-374a, or miR-382.

In certain embodiments of the present invention disclosed herein is a nucleic acid molecule or derivative that binds to miRNA and sequesters it inside of a muscle cell or other kind of cell.

In certain embodiments of the present invention disclosed herein is a nucleic acid molecule or derivative that increases the expression of dystrophin protein in muscle cells.

In certain embodiments of the present invention disclosed herein is a nucleic acid molecule or derivative that increases the expression of dystrophin protein in muscle cells.

In certain embodiments of the present invention disclosed herein is a nucleic acid molecule or derivative that binds to miR-146a.

In certain embodiments of the present invention disclosed herein is a nucleic acid molecule or derivative that binds to miR-146b-5p.

In certain embodiments of the present invention disclosed herein is a nucleic acid molecule or derivative that binds to miR-223.

In certain embodiments of the present invention disclosed herein is a nucleic acid molecule or derivative that binds to miR-320a.

In certain embodiments of the present invention disclosed herein is a nucleic acid molecule or derivative that binds to miR-374a.

In certain embodiments of the present invention disclosed herein is a nucleic acid molecule or derivative that binds to miR-382.

In certain embodiments of the present invention disclosed herein is a pharmaceutical composition comprising a nucleic acid molecule or derivative as disclosed herein and a pharmaceutically acceptable carrier or excipient.

In certain embodiments of the present invention disclosed herein is a covalent or non-covalent conjugate comprising the nucleic acid molecule or derivative as disclosed herein and a second targeting effector moiety.

In certain embodiments of the present invention disclosed herein is a nucleic acid molecule or derivative thereof able to functionally inactivate the action of miR-146a, miRNA-146b-5p, miR-223, miR-320a, miR374a, and/or miR-382 and increase dystrophin protein translation in muscle.

In certain embodiments of the present invention disclosed herein is a nucleic acid molecule or derivative thereof that binds to at least one miRNA selected from the group consisting of miR-146a, miRNA-146b-5p, miR-223, miR-320a, miR374a, and miR-382 by sequence complementarity and that selectively sequesters said miRNA in muscle cells.

In certain embodiments of the present invention disclosed herein is a nucleic acid molecule or derivative thereof, comprising one or more protector sequences complementary to miR-146a, miRNA-146b-5p, miR-223, miR-320a, miR374a, and/or miR-382 sequences on the 3'UTR of dystrophin; wherein the 3'UTR seed sequences of dystrophin bound by these miRNAs are selected from the group consisting of:

```
a. miR-146a:
                                       (SEQ ID NO: 16)
5'-UGAUUGUUCAUAAUACAUAAAGUUCUCUGUAAUUACAA
CUAAAUUAU-3' DMD b. miR-146b:
                                       (SEQ ID NO: 17)
5'-AUGAUUGUUCAUAAUACAUAAAGUUCUCUGUAAUUACAA
CUAAAUUA-3' DMD c. miR-223:
                                       (SEQ ID NO: 18)
5'-AAGUAUAUAAAUACUAUAGUUAUAUAGAUAAAGAGAU-3'
DMD d. miR-320a:
                                       (SEQ ID NO: 19)
5'-CAGGUACUGAGUUCUUACUUGAGUAUCAUAAUAU-3'
DMD e. miR-374a Site 1:
                                       (SEQ ID NO: 20)
5'-UUUGUGAAGGGUAGUGGUAUUAUACUGUAGAUU-3' DMD f. miR-374a Site 2:
                                       (SEQ ID NO: 21)
5'-AAUACACAGGACUUAUUAUAUCAGAGU-3' DMD
```

-continued

```
g. miR-374a Site 3:
                                    (SEQ ID NO: 22)
5'-CCAAAUAUAUGCCUUACUAUUGUAUUAUAGUACUGCU-3'
DMD h. miR-382:
                                    (SEQ ID NO: 23)
5'-AGCUCCAGAUGUUUCUCAUUUUAAACAACUUUCCACUGAC
AACGAAA-3' DMD
and c. miR-223:
                                    (SEQ ID NO: 18)
5'-AAGUAUAUAAAUACUAUAGUUAUAUAGAUAAAG
AGAU-3' DMD.
```

In certain embodiments of the present invention disclosed herein is a nucleic acid molecule or derivative thereof wherein at least one of the protector sequences for the group consisting of:

```
a. miR-146a:
                                    (SEQ ID NO: 24)
5'-ACAGAGAACTTTATGTATTATGAAC-3' b. miR-146b:
                                    (SEQ ID NO: 25)
5'-ACAGAGAACTTTATGTATTATGAAC-3' c. miR-320a:
                                    (SEQ ID NO: 26)
5'-ATGATACTCAAGTAAGAACTCAGTA-3' d. miR-374a Site 1:
                                    (SEQ ID NO: 27)
5'-ACAGTATAATACCACTACCCTTCAC-3' e. miR-374a Site 2:
                                    (SEQ ID NO: 28)
5'-CTGATATAATAAGTCCTGTGTATTC-3' f. miR-374a Site 3:
                                    (SEQ ID NO: 29)
5'-CAGTACTATAATACAATAGTAAGGC-3'
and g. miR-382:
                                    (SEQ ID NO: 30)
5'-CGTTGTCAGTGGAAAGTTGTTTAAA-3' DMD
``` or a protector sequence having 1, 2, 3, or 4 insertions, substitution, or deletions to said sequences.

In certain embodiments of the present invention disclosed herein is a nucleic acid molecule or derivative thereof that comprises two, three, four or more of said protector sequences that are complementary to said mRNAs.

In certain embodiments of the present invention disclosed herein is a nucleic acid molecule or derivative thereof wherein at least one nucleotide is not complementary to the corresponding nucleotide comprised in the region from nt 9 to nt 14 of SEQ ID NOs:16-23.

In certain embodiments of the present invention disclosed herein is a nucleic acid molecule or derivative thereof wherein at least three nucleotides are not complementary to the corresponding nucleotide comprised in the region from nt 9 to nt 14 of SEQ ID NOs:16-23.

In certain embodiments of the present invention disclosed herein is a nucleic acid molecule or derivative thereof that is able to compete with at least one miRNA selected from the group consisting of miR-146a, miRNA-146b, miR-223, miR-320a, miR374a, and miR-382 for binding to the 3'UTR dystrophin mRNA.

In certain embodiments of the present invention disclosed herein is a nucleic acid molecule or derivative thereof comprising a sequence that is complementary to the 3'UTR dystrophin mRNA region which is recognized by a miRNA selected from the group consisting of miR-146a, miRNA-146b, miR-223, miR-320a, miR374a, and/or miR-382 sequences SEQ ID NOs:16-23.

In certain embodiments of the present invention disclosed herein is a nucleic acid molecule or derivative thereof being a modified synthetic oligonucleotide.

In certain embodiments of the present invention disclosed herein is a nucleic acid molecule or derivative thereof belonging to the group of locked nucleic acids, methylated oligonucleotides, phosphoro-thiolated oligonucleotides, morpholino oligonucleotides, and poly-morpholino oligonucleotides.

In certain embodiments of the present invention disclosed herein is a method for increasing the translation of dystrophin in a patient in need thereof, comprising the administration of a therapeutically active amount of a nucleic acid molecule or derivative thereof as disclosed herein.

In certain embodiments of the present invention disclosed herein is a method for modulating the expression of dystrophin comprising contacting a cell expressing mRNA encoding dystrophin with the nucleic acid or derivative as disclosed herein.

In certain embodiments of the present invention disclosed herein is a method as disclosed herein further comprising administering the nucleic acid or derivative as disclosed herein to a subject having a dystrophin-related disease in an amount effective to increase the expression of dystrophin.

In certain embodiments of the present invention disclosed herein is a method as disclosed herein, wherein said dystrophin-related disease is muscular dystrophy.

In certain embodiments of the present invention disclosed herein is a method as disclosed herein, wherein said dystrophin-related disease is Becker muscular dystrophy.

In certain embodiments of the present invention disclosed herein is a method as disclosed herein, wherein said dystrophin-related disease is Duchenne muscular dystrophy.

In certain embodiments of the present invention disclosed herein is a method as disclosed herein, further comprising the treatment of said patient with a codon read through antisense therapy.

In certain embodiments of the present invention disclosed herein is a method as disclosed herein, further comprising the treatment of said patient with an exon skipping antisense therapy.

In certain embodiments of the present invention disclosed herein is a method as disclosed herein, further comprising the administration of VBP-15.

In certain embodiments of the present invention disclosed herein is the use of a therapeutically active amount of a nucleic acid molecule or derivative thereof as disclosed herein for increasing the translation of dystrophin in a patient in need thereof.

In certain embodiments of the present invention disclosed herein is the use of a nucleic acid or derivative as disclosed herein for modulating the expression of dystrophin comprising contacting a cell expressing mRNA.

In certain embodiments of the present invention disclosed herein is the use of a nucleic acid or derivative as disclosed herein in an amount effective to increase the expression of dystrophin.

In certain embodiments of the present invention disclosed herein is a use as disclosed herein, wherein said dystrophin-related disease is muscular dystrophy.

In certain embodiments of the present invention disclosed herein is a use as disclosed herein, wherein said dystrophin-related disease is Becker muscular dystrophy.

In certain embodiments of the present invention disclosed herein is a use as disclosed herein, wherein said dystrophin-related disease is Duchenne muscular dystrophy.

In certain embodiments of the present invention disclosed herein is a use as disclosed herein, further comprising the treatment of said patient with a codon read through antisense therapy.

In certain embodiments of the present invention disclosed herein is a use as disclosed herein, further comprising the treatment of said patient with an exon skipping antisense therapy.

In certain embodiments of the present invention disclosed herein is a use as disclosed herein, further comprising the administration of VBP-15.

Figure 1:
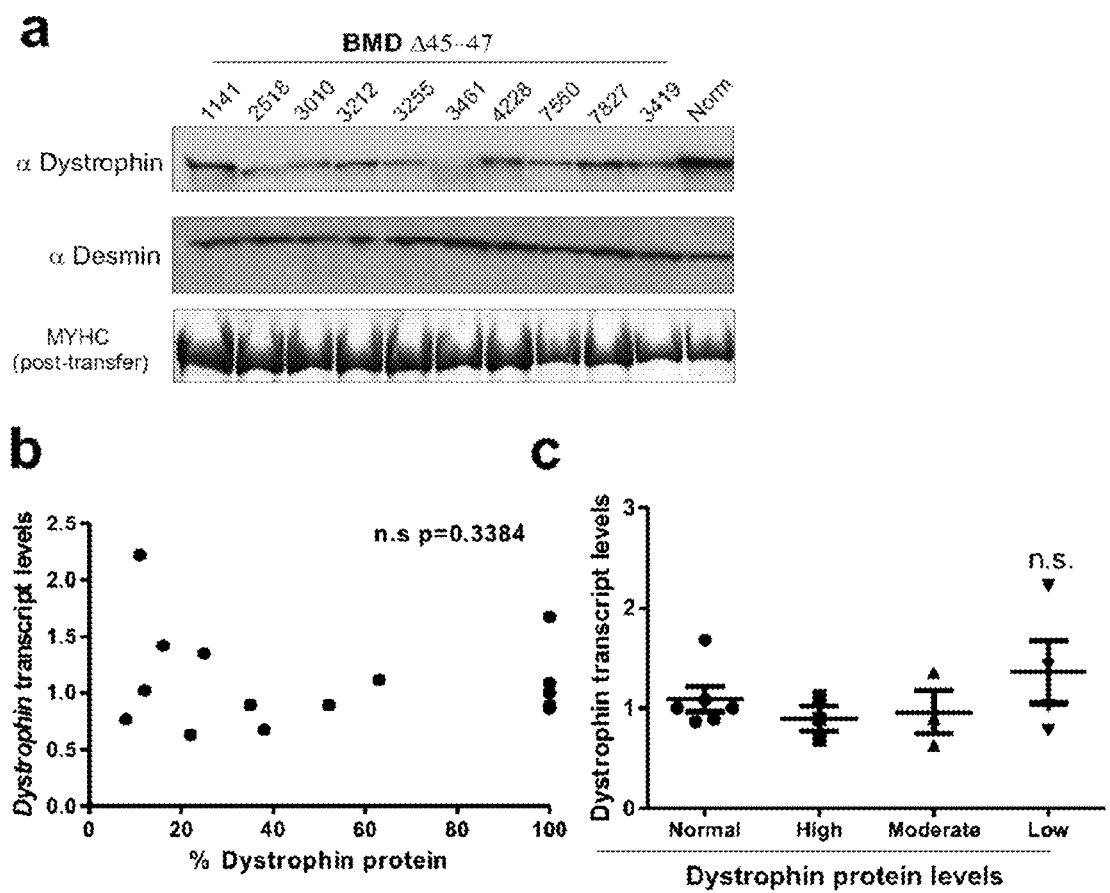
FIG. 1—Becker Muscular Dystrophy (BMD) patients with the same deletion mutation possess variable levels of dystrophin protein. (a) Western blot of BMD patient biopsies with a deletion mutation in exons 45-47 (BMD Δ45-47). 40 μg of each sample was used for analysis. Western analysis for desmin and Comassie staining for post-transfer myosin heavy chain (MYHC) are shown in lower panels to demonstrate equal loading. (b) Pearson's correlation of dystrophin transcript levels vs. percent dystrophin protein. (c) Dystrophin transcript levels of BMD patients stratified by dystrophin protein levels (as noted in Table 1). (a) and (b) collectively demonstrate no significant correlation between dystrophin transcript and protein levels.

DETAILED DESCRIPTION miRNAs that Inhibit Dystrophin Expression.

One aspect disclosed herein is the identification of the particular kinds of miRNA molecules that inhibit dytrophin expression. These include miR-146a, miR-146b-59, miR-223, miR-320a, miR-374a, and/or miR-382 and other species described herein. These molecules may be isolated or purified from their natural sources or synthesized. An animal miRNA may only be partially complementary to its mRNA target and can contain a "seed sequence" or "seed region," such as a 6-8 nucleotide sequence, near its 5' end that affects its mRNA target specificity.

Inhibitors of miRNAs (Protector Molecules, Antagomirs).

Another aspect disclosed herein is a molecule, in certain embodiments a nucleic acid molecule or modified nucleic acid molecule, that binds to and inhibits the miRNAs which inhibit or repress dystrophin expression. The nucleic acid protective molecules of the invention bind to partially or fully complementary sequences of the miRNAs which modulate or repress dystrophin expression. They may also be used to control the expression of other genes that are regulated by the same miRNAs that inhibit dystrophin expression.

The terms "protector molecule," "protector sequence," "antagomir," "molecule binding miRNA," or "molecule repressing miRNA" as used herein refer to molecules, which in certain embodiments are oligonucleotides, that bind to and decrease the inhibitory activity of miRNA that binds to a nucleic acid molecule encoding dystrophin. A protector or antagomir molecule may comprise a single sequence binding to an miRNA or multiple sequences binding to the same or different miRNAs. It may be single or double-stranded. Generally, these molecules can range in length from 10 nucleotide bases to 25 nucleotide bases and will bind to the portion of an miRNA that binds to a nucleic acid encoding dystrophin. However, longer or shorter protector or antagomer sequences may be used so long as they bind to an miRNA ad inhibit or modulate its activity, e.g., such as molecules having 6, 7, 8, 9, 10, 11, 12, 13, 14, 15, 16, 17, 18, 19, 20, 21, 22, 23, 24, 25, 26, 30, 35, 40, 50 or more nucleotide bases.

An example of a protector sequence that contains a sequence complementary to an miRNA is shown below. The seed sequence of miR-146a is 3'-UAAGUCAAGAG-5' (SEQ ID NO:31) and is complementary to the human dystrophin 3'UTR. A binding segment of a protector sequence corresponding to a miRNA seed sequence is shown below:

Seed sequence:
(SEQ ID NO: 31)
3'-UAAGUCAAGAG-5'
miRNA seed sequence complementary to dystrophin mRNA.

Protector sequence:
(SEQ ID NO: 32)
3'-AUUCAGUUCUC-5'
miRNA seed sequence complementary to dystrophin mRNA.

These terms encompass natural or synthetic or modified nucleic acids that are fully complementary to a target sequence, such as a particular miRNA sequence, as well as to those having a mismatch or 1, 2, 3, 4, 5, 6, 7, or 8 nucleotides which are not fully complementary, but which still hybridize or bind to the target miRNA. The inhibitory molecules of the present invention include oligonucleotides that have a sequence identity of at least 70%, 75%, 80%, 85%, 90%, 95%, 96%, 97%, 98%, or 99% or higher over a span of at least 10 continuous nucleotides. Sequence identity may be determined using nucleotide BLAST, which is incorporated by reference to the current version of this program at blast.ncbi.nlm.nih.gov/Blast.cgi?PROGRAM= blasm&BLAST_PROGRAMS=megaBlast&PAGE_TYPE= BlastSearch&SHOW_DEFAULTS=on&LINK_LOC= blasthome with the default parameters for short nucleotide sequences such as those below:

| Program | Word Size | Filter Setting | Expect Value |
|---|---|---|---|
| Standard nucleotide BLAST | 11 | On (Dust) | 10 |
| Search for short/near exact matches | 7 | Off | 1000 |

Modified Oligonucleotides.

The oligonucleotides of the present invention may contain one or more modified nucleotides and/or non-phosphodiester linkages. Chemical modifications well known in the art that increase stability, availability, and/or cell uptake of a nucleic acid molecule may be used. Examples of such modifications include phosphorothioate linkages, 2'-O-methylribonucleotides, 2'-deoxy-fluoro ribonucleotides, 2'-deoxy ribonucleotides, nucleotides containing a universal base, 5'-C-methyl nucleotides, and those described by Chemical modification and design of anti-miRNA oligonucleotides in Gene Therapy (2011) 18, 1111-1120; doi: 10.1038/gt2011.100; published online 14 Jul. 2011, which is hereby incorporated by reference. The compounds disclosed herein are not limited to these particular examples and any known chemical modifications may be employed for the molecules of the present invention so long as the resulting molecule retains the ability to bind to inhibit the activity of its target miRNA.

The oligonucleotides disclosed herein can be made using molecular biology and/or genetic engineering techniques to produce them recombinantly. The recombinant miRNAs or protector molecules are then isolated or purified using techniques known in the art. For example, a DNA expression vector encoding the miRNA or protector molecule may be transformed into a host cell, the transformed cell cultured under conditions where the miRNA or protector molecule is expressed, and the miRNA or protector molecule obtained from the cells or the culture medium, and then further isolated or purified. The host cell may be a human cell, a cell from a non-human mammal, or another kind of eukaryotic cell, such as a yeast cell like Saccharomyces cerevisiae, Schizosaccharomyces pombe, Kluyveromyces strains, Candida, or another yeast strain that can express miRNA or the protector molecule; or a prokaryotic cell, such as Escherichia coli or Bacillus subtilis. An expression vector containing the nucleic acid encoding the miRNA or protector molecule may be introduced into a host cell using known methods including by calcium phosphate transfection, DEAE or dextran mediated transfection, or electroporation. Such oligonucleotides may also be transformed into cells in vivo or used to produce transgenic animals.

Alternatively, an miRNA or protector molecule can be obtained synthetically, for example, by chemically synthesizing a nucleic acid by any method of synthesis known to the skilled artisan. Methods for chemical synthesis of nucleic acids include, but are not limited to, in vitro chemical synthesis using phosphotriester, phosphate, or phosphoramidite chemistry and solid phase techniques, or by deoxynucleoside H-phosphonate intermediates. A miRNA or protector molecule may also be replicated using well-known molecular biological techniques such as the polymerase chain reaction (PCR). Optionally, these molecules may be produced in forms that are more biologically stable, such as to have increased resistance to nucleases, or to enhance their uptake by a cell or tissue.

Antisense oligonucleotide (AO)-mediated exon skipping to convert an out-of-frame Duchenne Muscular Dystrophy (DMD) mutation into an in-frame Becker Muscular Dystrophy (BMD) mutation is considered one of the most promising therapeutic approaches for DMD. To date, studies in both human trials and the DMD dog model have shown success in recovering dystrophin, however the degree of success has been variable, both within a patient (different muscles or regions of muscle), and between patients. Related to this variability is the observed heterogeneity between BMD patients harboring the same in-frame mutation. We and others have noted that Becker muscular dystrophy patients harboring identical in-frame deletions may show quite different clinical phenotypes and amount of dystrophin protein in muscle biopsy. From our tissue biopsy bank, we identified 10 BMD patient muscle biopsies sharing the same exon 45-47 in-frame deletion mutation. There were marked differences between patients regarding the amount of dystrophin protein (5%-80%), histological severity, and clinical phenotype. Quantitation of mRNA splicing patterns and mRNA levels in these biopsies did not show correlation with dystrophin protein levels. Recent works describing microRNA dysregulation in several muscle disorders including DMD. Given this, we performed in silico analysis of the highly conserved DMD 3'UTR and identified 78 putative microRNA binding sites. This led us to test whether variability in levels of microRNAs targeting the dystrophin mRNA 3'UTR may underlie dystrophin protein variability observed in BMD biopsies and exon skipping trials. Using a microRNA profiling approach, an inverse correlation of BMD dystrophin levels and both the number of upregulated dystrophin-targeting microRNAs and the expression levels of those microRNAs were observed. To test the functional significance of the elevated microRNAs in regulating dystrophin mRNA, we transfected a dystrophin 3'UTR luciferase construct into C2C12 cells, and tested the effects of miR-146b, miR-374a, or miR-31. These microRNAs used singly or in combination showed strong inhibition of translation from the 3'UTR construct. In vivo, injection of a physiological relevant mix of miR-146b, miR-374a, and miR-31 into the tibialis anterior of BL-10 mice visibly decreased dystrophin protein levels. These data strongly suggested that miR-146b, miR-374a, and miR-31 play a role in the post-transcriptional regulation of dystrophin, and that alterations in the levels of these microRNAs may dictate the amount of dystrophin protein content in muscle. These results provide a basis for the identification of dystrophin-regulating microRNAs that 1) explain variability in and provide a screening tool for exon skipping trials; 2) provide novel targets for AO combination therapies; and 3) provide targets for the development of antagomirs as a novel BMD therapy.

EXAMPLES

Materials and Methods

Sequences of miRNAs Under Analysis

The following mature miRNA sequences were analyzed. These show a high degree of conservation between their murine and human versions. Seed sequences of these miRNAs that are complementary to a sequence in the 3'UTR of human dystrophin mRNA are underlined.

1. hsa-miR-146a, mmu-miR-146a, Sequences 100% Complementary

```
hsa-miR-146a
                                 (SEQ ID NO: 1)
3'-UUGGGUACCUUAAGUCAAGAGU-5'
```

The underlined sequences below refer to a sequence complementary to the human dystrophin 3'-UTR in 3 identified binding site.

```
Seed Sequence:
                                 (SEQ ID NO: 2)
3'-uuggguaccuUAAGUCAAGAGu-5'
```

2. hsa-miR-146b-5p, mmu-miR-146b, Sequences 100% Complementary

```
hsa-miR-146b-5p
                                 (SEQ ID NO: 3)
3'-UCGGAUACCUUAAGUCAAGAGU-5'
```

The underlined sequences below refer to a sequence complementary to the human dystrophin 3'-UTR in 3 identified binding site.

```
Seed Sequence:
                                 (SEQ ID NO: 4)
3'-ucggauaccuUAAGUCAAGAGu-5'
```

3. hsa-miR-223, mmu-miR-223, 100% Complementary

```
Human Sequence
hsa-miR-223
                                 (SEQ ID NO: 5)
3'-ACCCCAUAAACUGUUUGACUGU-5'
```

The underlined sequences below refer to a sequence complementary to the human dystrophin 3'-UTR in 3 identified binding site.

```
Seed Sequence:
                                            (SEQ ID NO: 6)
3'-acccCAUAAACUGUUUGACUGu-5'
```

4. hsa-miR-320a, mmu-miR-320, 100% Complementary

```
hsa-miR-320a
                                            (SEQ ID NO: 7)
3'-AGCGGGAGAGUUGGGUCGAAAA-5'
```

The underlined sequences below refer to a sequence complementary to the human dystrophin 3'-UTR in 3 identified binding site.

```
Seed Sequence:
                                            (SEQ ID NO: 8)
3'-agcgggagaguugggUCGAAAa-5'
```

5. hsa-miR-374a, mmu-miR-374b (2 bp changes)

```
Human Sequence
hsa-miR-374a
                                            (SEQ ID NO: 9)
3'-GUGAAUAGUCCAACAUAAUAUU-5'

Mouse Sequence
mmu-miR-374b
                                            (SEQ ID NO: 10)
3'-GUGAAUCGUCCAACAUAAUAUA-5'
```

The underlined sequences below refer to a sequence complementary to the human dystrophin 3'-UTR in 3 identified binding site.

```
Seed Sequence 1:
                                            (SEQ ID NO: 11)
3'-gugaauaguCAACAUAAUAUu-5'

Seed Sequence 2:
                                            (SEQ ID NO: 12)
3'-gugaauaGUCCAACAUAAUAUu-5'

Seed Sequence 1:
                                            (SEQ ID NO: 13)
3'-guGAAUAGUCCAACAUAAUAUu-5'
```

6. hsa-miR-382, mmu-miR-382, 100% Complementary

```
hsa-miR-382
                                            (SEQ ID NO: 14)
3'-GCUUAGGUGGUGCUUGUUGAAG-5'
```

The underlined sequences below refer to a sequence complementary to the human dystrophin 3'-UTR in 3 identified binding site.

```
Seed Sequence:
                                            (SEQ ID NO: 15)
3'-gcuuaGGUGGUGCUUGUUGAAg-5'
```

Muscle Biopsies

6 BMD muscle biopsies were obtained from the Telethon Biobank from Dr. Angelini Corrado (ID#s: 2518, 3010, 3419, 4228, 7560, 7827). The remaining 4 BMD muscle biopies were obtained in-house from our muscle biopsy bank as previously reported (ID#s: 1141, 3212, 3255, 3461) (Kesari et al, 2008). Additionally, 5 DMD muscle biopsies were obtained in-house from our muscle biopsy bank (ID#s: 1179, 1518, 2069, 3168, 4177). Normal human muscle biopsies: Total protein extracts of muscle biopsies from healthy subjects were obtained from Dr. David Rowlands at Massey University, Wellington, New Zealand as previously reported (Brown et al, 2013). Biopsy samples from the GRMD or WT dogs were obtained from Joe Kornegay—the CS, and VL muscles were collected surgically and subsequently archived at −80° C. until analysis as previously reported (Nghiem et al, 2013).

Cell Lines

C2C12 Cells:

C2C12 mouse myoblasts (American Type Culture Collection (ATCC), Manassas, Va.) were cultured at 37° C., 5% $CO_2$ in DMEM (Invitrogen) supplemented with 20% fetal bovine serum, 200 mml-glutamine, 10 units/ml penicillin, and 10 µg/ml streptomycin.

Immortalized Human Myoblasts:

Immortalized human myoblasts were obtained from Dr. Vincent Mouly, PhD (Institut de Myologie, Paris, France) (Mamchaoui et al, 2011). Cells were cultured at 37° C., 5% $CO_2$ using the Skeletal Muscle Cell Growth Medium Kit (Promocell) adjusted to 20% FBS. For differentiation, cells were seeded cells 48 hrs before in growth medium on gelatin (0.5%) coated dishes. 24 hours post-transfection, cells were cultured in Differentiation medium consisting of DMEM (Invitrogen), 50 µg/ml Gentamycin (Invitrogen), 10 µg/ml bovin Insulin (Sigma) and 100 µg/ml of human Apotransferrin (Sigma). Stock solutions were prepared in DMEM and filter sterilized. Differentiation was carried out for 6 days.

Western Blot Analysis

Muscle proteins from cryosections were extracted with lysis buffer containing 75 mM Tris-HCl (pH 6.8), 10% sodium dodecyl sulfate, 10 mM EDTA, and 5% 2-mercaptoethanol as previously described (Yokota et al, 2009). 40 µg proteins were loaded onto a 3-8% Tris-Acetate gel (Bio-Rad). The gels were transferred onto a nitrocellulose membrane overnight at 20V, 4° C., followed by a 1 h. pulse the next day at 80V. A combination of DYS-1+DYS-2 (Novocastra) antibodies against dystrophin, along with a polyclonal antibody desmin was used as primary antibodies. The post-transfer gel was stained using Bio-safe Comassie (Bio-Rad). Horseradish peroxidase-conjugated anti-mouse or anti-rabbit goat immunoglobulin (Millipore) was used as secondary antibodies. Enzyme chemiluminescence kit (Pierce) was used for the detection. Blots and stained gels were analyzed by Bio-Rad densitometry software. For BMD samples, both dystrophin bands and MYHC bands were measured by densitometry. MYHC levels were determined as a ratio of BMD/Normal to determine a correction factor. The intensity of dystrophin bands in each sample was measured and normalized by diving by the calculated correction factor. Standard curve is shown using 40 (100%), 20 (50%), 8 (20%), 4 (10%), and 2 µg (5%) of protein extracted from normal healthy muscle lysate. Percent dystrophin was calculated by substituting the calculated intensity value for each sample into the Standard curve equation of 40 (100%), 20 (50%), 8 (20%), 4 (10%), and 2 µg (5%) (% dystrophin=4.12x−5.22) and values are shown in FIG. 1b,c.

RNA Preparation and Analysis

Human Samples microRNA:

20 mg frozen muscle was homogenized in TriZol reagent (Invitrogen), followed by RNA extraction. miRNA profiles were determined using The TaqMan low-density Arrays A (TaqMan® Array Human MicroRNA A v2.1 Card Set, Applied Biosystems, Life Technologies). These analyses were performed on RNA extracted from 10 BMD Samples, 6 controls and 5 DMD samples.

Single-stranded cDNA was synthesized from 100 ng of total RNA using the TaqMan® MicroRNA Reverse Transcription Kit (Applied Biosystems, Life Technologies, Poland) and highly multiplexed RNA-specific stem-looped Megaplex RT Primers, Human Pool A v2.1 (Applied Biosystems, Life Technologies, Poland), according to the manufacturer's protocol. Preamplification was then performed using Taqman Pre-amp master mix (Life technologies) according to the manufacturer's instructions. 9 ul of the pre-amp product was added to 450 ul TaqMan universal master mix No AmpErase UNG (2×) and then brought to a total volume of 900 ul using nuclease-free water. After brief mixing and centrifugation, the mixture was transferred into one of the eight loading ports on a micro fluidic card and were centrifuged and sealed according to manufacturer's instructions. Each card was placed in the micro fluidic card sample block of an ABI Prism® 7900HT sequence detection system (Applied Biosystems, Life Technologies, Poland), and PCR amplification was performed. The raw Ct values were calculated using RQ manager software v1.2.1 (ABI) and fold changes were subsequently calculated using the comparative cycle threshold $2(-\Delta\Delta C(T))$ method by choosing one control as the calibrator (Livak & Schmittgen, 2001).

Human Samples mRNA:

RNA from human samples was synthesized into cDNA using qscript (Quanta) and Taqman assays for dystrophin were used to measure dystrophin (DMD) mRNA levels using a Taqman assay for titin (TTN) (Life Technologies) as a muscle-specific control.

Mouse Samples microRNA:

20 mg frozen muscle was homogenized in TriZol reagent (Invitrogen), followed by RNA extraction. microRNAs were quantified with 7900HT Fast Real-Time PCR system using mouse-specific TaqMan microRNA assays with U6 snRNA as a control. Results were calculated as above using the $2(-\Delta\Delta C(T))$ method (Schmittgen, 2001).

Mouse Sample mRNA:

dystrophin levels were determined as in human samples above, this time using a taqman assay specific to mouse dystrophin (dmd).

Dog Samples microRNA:

20 mg frozen muscle was homogenized in TriZol reagent (Invitrogen), followed by RNA extraction. microRNAs were quantified with 7900HT Fast Real-Time PCR system using dog-specific TaqMan microRNA assays with U6 snRNA as a control. Results were calculated as above using the $2(-\Delta\Delta C(T))$ method (Schmittgen, 2001).

Immunofluorescence

Sections of 7 μm were cut from at least two-thirds of muscle length of tibialis anterior, at 100-1 μm intervals. Sections were air-dried, hydrated in PBS, and then subjected to immunofluorescence. All sections were incubated for 30 min with normal goat serum (1:20). The sections were then examined for dystrophin expression using the polyclonal antibody P7 against carboxyl-terminal dystrophin (Fairway Biotech) for 1 h at RT, 1:400 (Lu et al, 2000). After minutes washing with PBS, goat anti-rabbit IgG Alexa 594 1:400 was applied to sections for 45 min at RT. Sections were counter-stained with 4',6-diamidino-2-phenylindole (DAPI). Stained sections were mounted, coverslipped, and then imaged using the Zeiss ApoTome.2 microscope with 10× magnification. Microscope pictures were analyzed using Image J software (National Institutes of Health). Pictures were set to a threshold of 70 pixels, and then converted to a binary image and total/average pixels were measured.

Cloning

The entire 2.7 kb 3'UTR of dystrophin was amplified from normal muscle using the Flex cDNA synthesis kit (Quanta) using primers that added 5' XhoI and 3' NotI restriction enzyme sequences. The amplified product was gel purified, digested with XhoI and NotI, and ligated into the pSiCheck2 plasmid (Promega). Ligation productions were transformed into TOP10 cells (Life Technologies) using ampicillin selection. Positive clones were verified by diagnostic digests and Sanger sequencing.

Transfection Studies

Luciferase Assay:

C2C12 myoblasts were seeded in 24-well plates at a density of $4 \times 10^4$ cells/well. 24 h post-plating cells were co-transfected with 200 ng of Dys 3'UTR reporter along with 50 nM control of the indicated microRNA mimics (Life Technologies) using lipofectamine 2000. 24 h. post-transfection cells were harvested the assay were performed according to the Dual-Glow Luciferase Reporter Assay System protocol (Promega) using *Renilla* Luciferase (hR-Luc) as the readout. Results were normalized to an internal control (hLuc+) driven by a separate promoter within the reporter plasmid.

microRNA Transfections in Immortalized Human Myoblasts:

Immortalized human myoblasts were seeded on 0.4% Gelatin in 6-well plates at a density of $2.5 \times 10^5$ cells/well using skeletal muscle proliferation media as stated in Cell Culture methods above. 24 h. post-plating cells were co-transfected with 50 nM of the indicated microRNA mimics using lipofectamine 2000. 24 h post-transfection cells were switched to differentiation media with xx % HS. After 5 days of differentiation cells were lysed in dystrophin lysis buffer (Yokota et al, 2009) and western blot analysis was performed at stated in Western blot methods above.

In Vivo Mouse microRNA Injections

Intramuscular microRNA mimic injection: (C57BL/10Sc-SnJ) mice (The Jackson Laboratories) aged 6 weeks were used for intramuscular injections (n=6). 1.5 μg microRNA mimic in saline (Life Technologies) was injected into the tibialis anterior (TA) of mice, while a CTRL sequence was injected into the contralateral tibialis anterior (6 μL total volume). The muscles were harvested 7-days post-injection. Harvested TA muscles were immediately snap frozen in liquid-nitrogen cooled isopentane and stored at −80° C.

Notexin-Induced Muscle Damage Followed by microRNA Mimic Injection:

6 week-old (C57BL/6ScSnJ) were utilized for experiments (The Jackson JAX Laboratories) n=3. Muscle regeneration was induced by injecting 6 week-old C57BL6 (WT) mice with a bilateral intramuscular injection of 10 ul of 10 μg/ml of notexin per muscle. To do this, the tibialis anterior (TA) was surgically exposed (incisions are <1 cm in length) and tattoo dye was utilized to mark the location of the injection in the muscle. Skin was closed with sutures (5-0 prolene sutures) instead of surgical clips to minimize pain and tissue damage when reopening for the second injection. Three days post-injection, 10 ug of each microRNA mimic was injected into the right TA of mice with a scrambled control mimic (CTRL) was injected into the contralateral (Left) TA. 7 days post-injection mice were sacrificed using $CO_2$ confirmed with cervical dislocation. The TA muscles were isolated and flash frozen in isopentane cooled in liquid nitrogen for experiments.

Systemic Delivery of PMOs to mdx23 Mice

Six mdx mice (C57BL/10ScSn-Dmd<mdx>/J (The Jackson Laboratories) were given a single 800 mg/kg dose of PMO (Gene Tools, Philomath, Oreg.): 5'-GGCCAAAC- CTCGGCTTACCTGAAAT-3' (SEQ ID NO:33); administered through a retro-orbital injection into the right eye. As a control, six additional mice were injected with saline in the same manner and eye as the PMO injected mice. After one month, mice were euthanized via carbon dioxide inhalation. Tibialis anterior, gastrocnemius, triceps, quadriceps, heart and diaphragm muscles were harvested, snap-frozen in liquid nitrogen-cooled isopentane, and stored at −80° C. for later processing. For analysis, dystrophin protein levels and microRNA levels in mice were compared to age-matched WT controls (C57BL/10ScSnJ) The Jackson Laboratories).

Systemic Delivery of VBP15 and Prednisone to mdx23 Mice

Mdx23 (C57BL/10ScSn-Dmd<mdx>/J) mice (The Jackson laboratories) were dosed with 5 mg/kg prednisolone or 15 mg/kg cherry syrup as previously reported (Heier et al, 2013).

Results

TABLE 1

The dystrophin 3'UTR contains 78 putative microRNA binding sites

| MicroRNA | Binding site(s) (start of 3'UTR) | MicroRNA | Binding site(s) (start of 3'UTR) |
|---|---|---|---|
| hsa-miR-340 | 102, 326, 359, 400, 417, 2011, 2399 | hsa-miR-30e | 146 |
| hsa-miR-374a | 185, 986, 2628 | hsa-miR-361-5p | 1944 |
| hsa-miR-374b | 185, 986, 2628 | hsa-miR-194 | 1784 |
| hsa-miR-410 | 694 | hsa-miR-448 | 255 |
| hsa-miR-186 | 323, 2018, 2397 | hsa-miR-124 | 2614 |
| hsa-miR-139-5p | 192 | hsa-miR-506 | 2613 |
| hsa-miR-873 | 1943 | hsa-miR-490-3p | 1529 |
| hsa-miR-144 | 191 | hsa-miR-381 | 2622 |
| hsa-miR-190 | 2588 | hsa-miR-300 | 2622 |
| hsa-miR-190b | 2589 | hsa-miR-214 | 1049 |
| hsa-miR-153 | 253 | hsa-miR-494 | 892 |
| hsa-miR-211 | 955 | hsa-miR-129-5p | 268 |
| hsa-miR-204 | 952 | hsa-miR-495 | 2260 |
| hsa-miR-9 | 2052 | hsa-miR-875-5p | 1132 |
| hsa-let-7i | 1920 | hsa-miR-101 | 191 |
| hsa-let-7e | 1920 | hsa-miR-758 | 2585 |
| hsa-let-7g | 1920 | hsa-miR-31 | 316 |
| hsa-let-7b | 1921 | hsa-miR-103 | 2350 |
| hsa-let-7a | 1920 | hsa-miR-107 | 2350 |
| hsa-let-7c | 1921 | hsa-miR-497 | 1053 |
| hsa-miR-98 | 1921 | hsa-miR-15a | 1052 |
| hsa-let-7f | 1920 | hsa-miR-15b | 1052 |
| hsa-let-7d | 1920 | hsa-miR-16 | 1051 |
| hsa-miR-26a | 2497 | hsa-miR-195 | 1054 |
| hsa-miR-26b | 2495 | hsa-miR-424 | 1052 |
| hsa-miR-146a | 1267 | hsa-miR-205 | 171 |
| hsa-miR-146b-5p | 2499 | hsa-miR-375 | 2329 |
| hsa-miR-1297 | 655 | hsa-miR-320a | 2343 |
| hsa-miR-203 | 907 | hsa-miR-320b | 2343 |
| hsa-miR-382 | 143 | hsa-miR-320c | 2345 |
| hsa-miR-30a | 143 | hsa-miR-320d | 2346 |
| hsa-miR-30b | 143 | hsa-miR-223 | 726 |
| hsa-miR-30d | 143 | hsa-miR-590-3p | 357 |
| hsa-miR-30c | 143 | | |

TABLE 2

Stratification of BMD patient samples based on Dystrophin protein levels

| Patient ID | Percent Dystrophin | Category |
|---|---|---|
| 2518 | 12 | Low |
| 3010 | 16 | Low |
| 3255 | 8 | Low |
| 3461 | 11 | Low |
| 1114 | 35 | Moderate |
| 3212 | 22 | Moderate |
| 7560 | 25 | Moderate |
| 4228 | 38 | High |
| 7827 | 52 | High |
| 3419 | 63 | High |

TABLE 3

The number of dystrophin-targeting microRNAs is inversely correlated with dystrophin protein levels

| microRNA | p-value | FC |
|---|---|---|
| LOW | | |
| hsa-miR-146b-5p | 0.0059 | 17.61 |
| hsa-miR-382 | 0.0131 | 8.88 |
| hsa-miR-410 | 0.0032 | 6.71 |
| hsa-miR-758 | 0.0008 | 4.48 |
| hsa-miR-214 | 0.0003 | 4.35 |
| hsa-miR-494 | 0.0012 | 3.60 |
| hsa-miR-223 | 0.0053 | 3.48 |
| hsa-miR-146a | 0.0017 | 3.06 |
| hsa-miR-195 | 0.0012 | 2.61 |
| hsa-miR-374a | 0.0004 | 2.61 |
| has-miR-103 | 0.0015 | 2.09 |
| hsa-miR-320a | 0.0294 | 1.96 |
| let-7d | 0.0126 | 1.76 |
| let-7a | 0.0492 | 1.53 |
| MODERATE | | |
| hsa-miR-15b | 0.0002 | 7.04 |
| hsa-miR-223 | 0.0047 | 5.24 |
| hsa-miR-758 | 0.0139 | 4.79 |
| hsa-miR-214 | 0.0218 | 3.98 |
| hsa-miR-194 | 0.0159 | 3.60 |
| hsa-miR-16 | 0.0008 | 3.49 |
| hsa-miR-190 | 0.0112 | 3.02 |
| hsa-miR-195 | 0.0152 | 2.81 |
| miR-103 | 0.0302 | 2.09 |
| HIGH | | |
| hsa-miR-410 | 0.0282 | 4.6403 |
| hsa-miR-758 | 0.0038 | 3.6412 |
| hsa-miR-214 | 0.0241 | 2.6331 |
| hsa-miR-494 | 0.0326 | 2.394 |

TABLE 4

A subset of dystrophin targeting microRNAs is upregulated both in DMD patients and in BMD patients with low dystrophin levels

| LOW | | | DMD | | |
|---|---|---|---|---|---|
| microRNA | p-value | FC | microRNA | p-value | FC |
| hsa-miR-146b-5p | 0.0059 | 17.61 | hsa-miR-146b-5p | 0.0065 | 25.09 |
| hsa-miR-382 | 0.0131 | 8.88 | hsa-miR-382 | 0.0417 | 3.70 |
| hsa-miR-758 | 0.0008 | 4.48 | hsa-miR-758 | 0.0324 | 4.18 |
| hsa-miR-214 | 0.0003 | 4.35 | hsa-miR-214 | 0.0092 | 7.26 |
| hsa-miR-494 | 0.0012 | 3.60 | hsa-miR-494 | 0.0274 | 5.65 |
| hsa-miR-223 | 0.0053 | 3.48 | hsa-miR-223 | 0.3312 | 5.09 |
| hsa-miR-146a | 0.0017 | 3.06 | hsa-miR-146a | 0.4047 | 1.48 |
| hsa-miR-374a | 0.0004 | 2.61 | hsa-miR-374a | 0.0487 | −1.95 |
| hsa-miR-320a | 0.0294 | 1.96 | hsa-miR-320a | 0.0892 | 1.62 |
| has-miR-31 | 0.1236 | 2.16 | has-miR-31 | 0.0351 | 6.63 |

Figure 9:
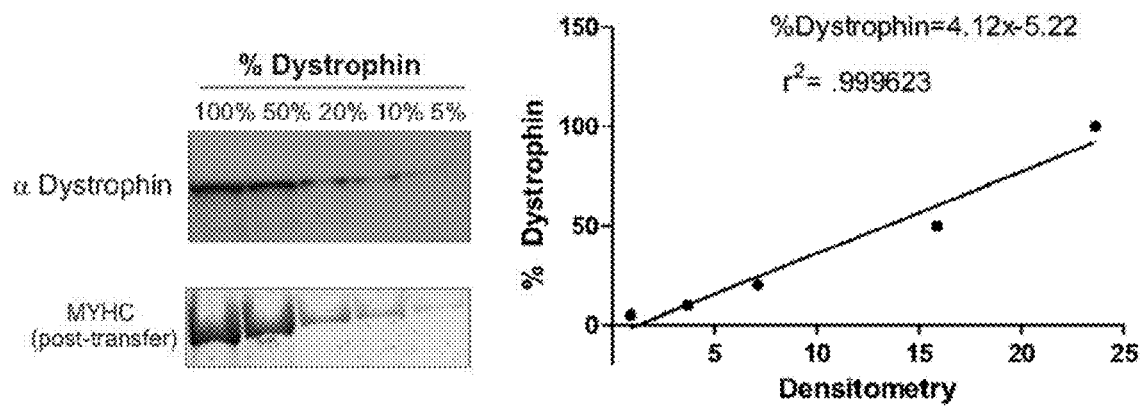
FIG. 9—Standard curve to calculate percent dystrophin in BMD samples. Right panel; Western blot analysis of normal healthy control muscle samples. 40, 20, 8, 4, and 2 μg of normal healthy control sample were loaded on the same gel as FIG. 1a to use as a standard curve for dystrophin quantification. Left panel; Graphical representation of standard curve. Densitometry was performed, and is plotted as percent dystrophin vs. band intensity.

Becker Muscle Harboring Same Exon 45-47 Deletion Mutation Possess Variable Dystrophin Levels Frozen muscle biopsies from 10 Becker muscular dystrophy patients sharing the same exon 45-47 in-frame deletion mutation were studied (BMD Δ45-47). Western blot analysis of patient muscle showed variable protein levels (FIG. 1a). Dystrophin levels were quantitated using a standard curve of normal healthy control muscle were loaded on the same gel (FIG. 9; $r^2$=0.999623). Using this, we determined that BMD Δ45-47 patient muscle possessed anywhere from 8%-63% dystrophin as compared to control (Table 2). Based on these calculations, patients were stratified into "Low", "Moderate" or "High" categories based on their levels of dystrophin.

We tested if variable dystrophin mRNA levels correlated with protein levels. Dystrophin mRNA was quantitated in the same biopsies by quantitative TaqMan RT-PCR assays relative to internal control transcripts. This showed that all biopsies showed similar levels of dystrophin mRNA, without any significant correlation to dystrophin protein levels (FIG. 1). We also used RT-PCR to determine if patients showed alternatively spliced transcripts around the novel exon 44-exon 48 junction, but no evidence of alternative splicing around the shared deletion was observed.

Figure 2:
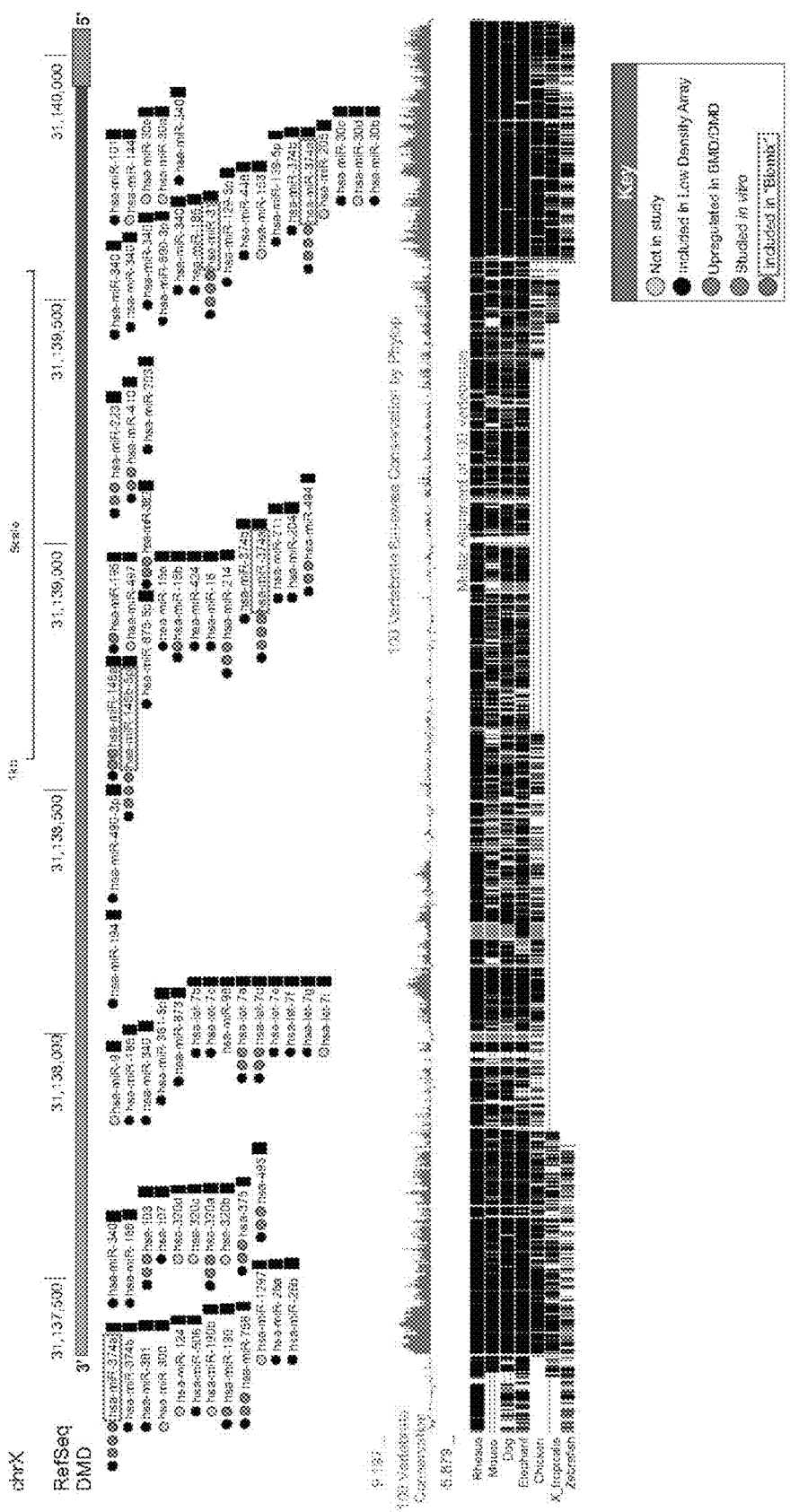
FIG. 2—The highly conserved dystrophin 3'UTR contains 78 microRNA binding sites. Schematic of the dystrophin 3'UTR (shown in the 3'-5' orientation). As shown in the mammalian conservation diagram, both ends are highly conserved among mammalian species (figure obtained from the UCSC genome browser). All 78 highly conserved microRNA binding sites are shown where an unfilled dot indicates a microRNA that was not included in the study, black indicates a microRNA that was found in the low density microRNA array, horizontal gray striped dot represents those microRNA that were found to be upregulated in BMD/DMD, vertical gray striped dot represents microRNAs studied in vitro and pattern filled dot indicates microRNAs included in the biomix.

Inverse Correlation Between Dystrophin Protein and Putative Dystrophin-Binding microRNAs The dystrophin 3'UTR is unusually long (2.7 kb) and particularly highly conserved among species, suggesting potential microRNA binding sites. We identified 78 potential microRNA binding sites, most in highly conserved subregions of the 3'UTR (FIG. 2, Table 1). We hypothesized that variable levels of microRNAs targeting the dystrophin mRNA could be a source of variable dystrophin protein levels in BMD Δ45-47 muscle. MicroRNA profiling was performed using RNA extracted from 5 control muscle samples with no known muscular dystrophies and from 10 BMD Δ45-47 muscle stratified into "Low" "Moderate" and "High" dystrophin levels (Table 2). We additionally performed microRNA profiling on RNA extracted from 6 Duchenne muscular dystrophy (DMD; loss of dystrophin) patient samples. TaqMan MicroRNA Array v3.0 A card querying 382 human microRNAs were utilized.

Figure 3:
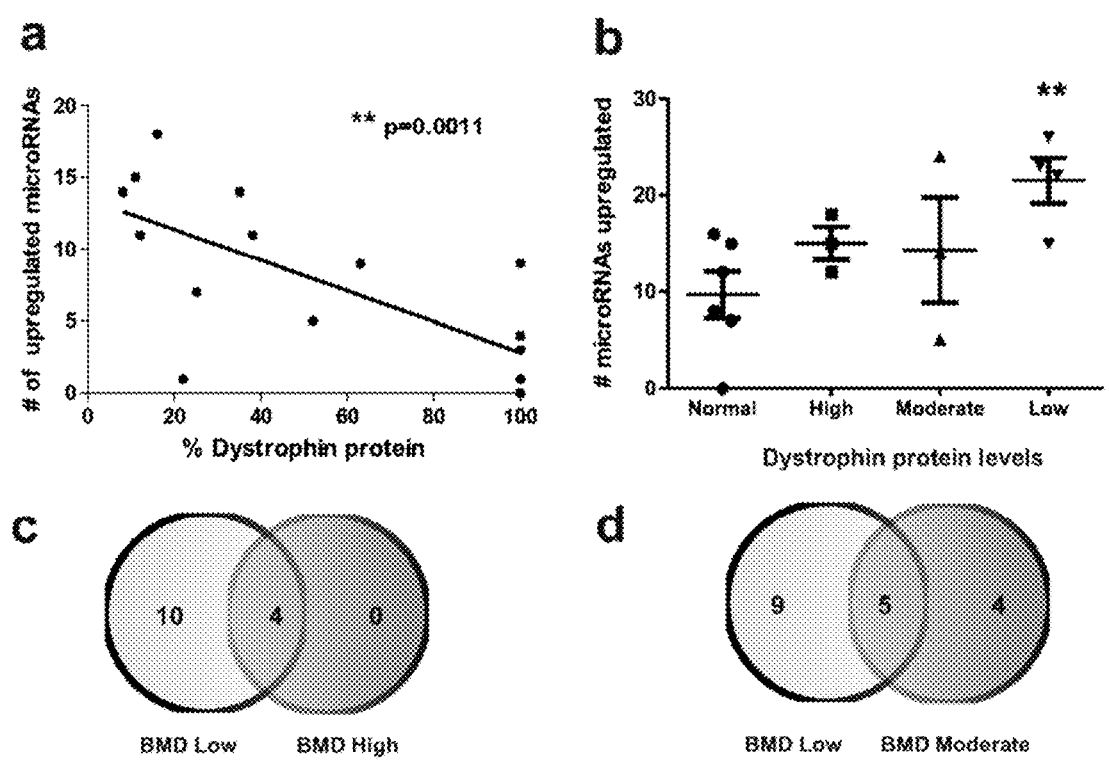
FIG. 3—The number of dystrophin-targeting microRNAs is inversely correlated with dystrophin protein levels. A low-density microRNA array (Taqman Low Density MicroRNA Array, TLDA) was performed to measure levels of microRNAs in normal and BMD Δ45-47 patients. Data was imported into RQ manager and results were normalized to the values of a selected normal calibrator. Data was then exported into Partek Genomics suite 5.0 for statistical analysis. P-values were determined using a One-Way ANOVA ($p<0.05$). (a) Pearson's correlation plotting number of upregulated microRNAs identified in microRNA array vs. percent dystrophin protein. Upregulated microRNAs were counted based on an increase of 1.6 or greater in each sample. (b) BMD patient samples were grouped into high, moderate and low in accordance with their respective dystrophin levels as described in Table 1. Graph depicts the number of upregulated microRNAs detected in each group. (c) Venn diagram demonstrating the number of upregulated microRNAs detected in either BMD low or BMD high vs. normal healthy control where the overlap shows those microRNAs that were shared among groups. (d) Venn diagram demonstrating the number of upregulated microRNAs detected in either BMD low or BMD moderate vs. normal healthy control where the overlap shows those microRNAs that were shared among groups.
Figure 10:
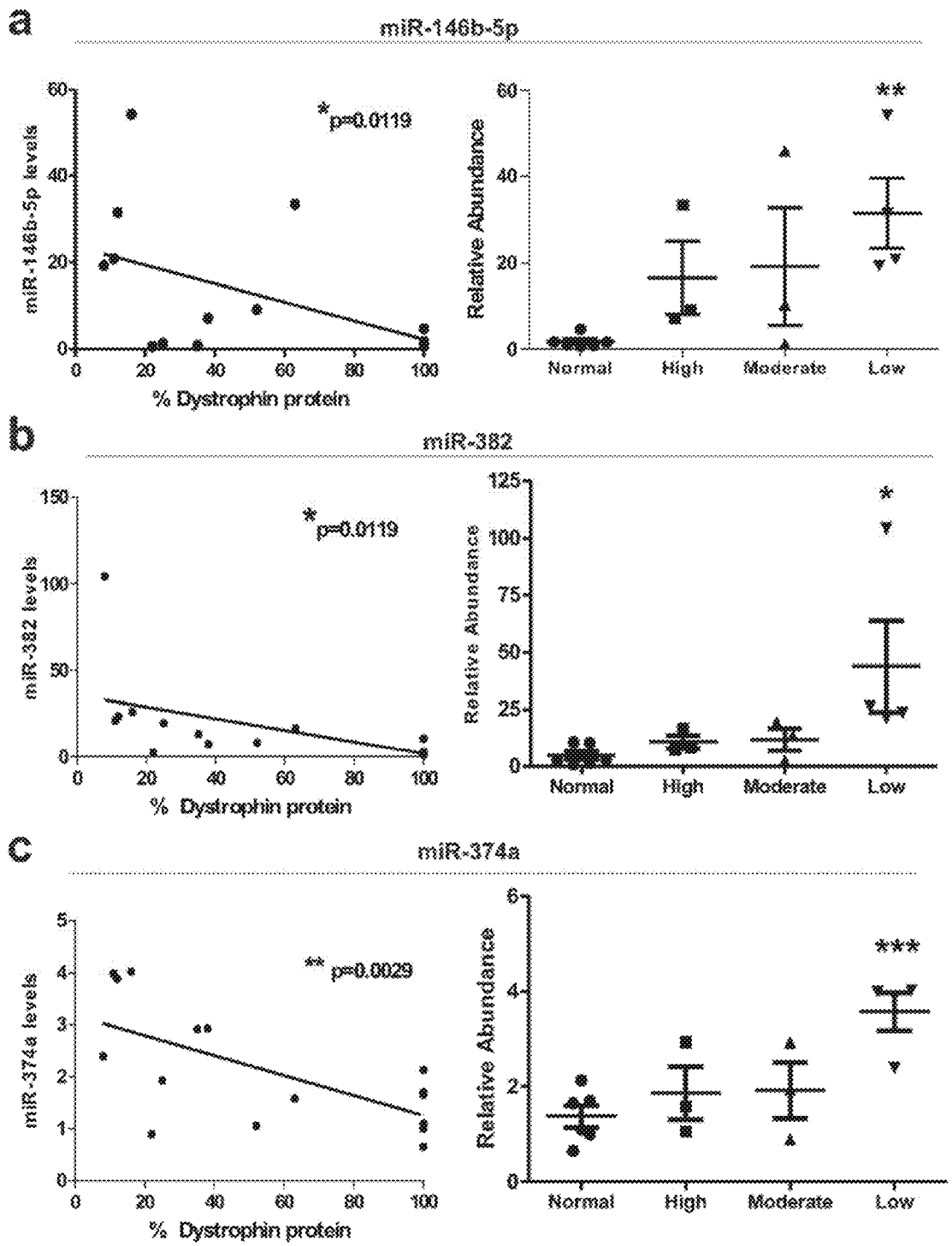
FIG. 10—The levels of dystrophin-regulating microRNAs are inversely proportional to dystrophin protein levels. All data is from the low density microRNA analysis. (a-c left panels) Graphs showing the levels of 3 respective microRNAs from low density microRNA array (miR-146b, miR-382, miR-374a plotted against percent dystrophin protein. Linear regression and Pearson's correlation analyses were then performed. The best fit line for each graph is shown in blue and the p-value corresponding to each correlation score is shown in orange. (a-c, right panels) The relative abundance of microRNAs was plotted according to dystrophin levels as grouped in Table 1. Statistical analysis was performed in Partek Genomics Suite (One-way ANOVA; $*p<0.05$; $p<0.01$; $*p<0.001$.)
Figure 11:
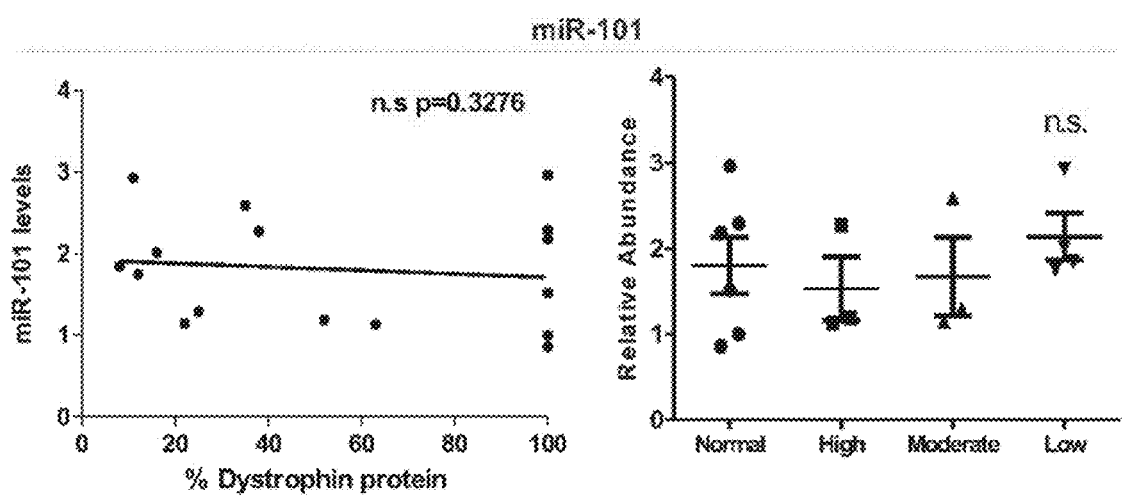
FIG. 11—Not all putative dystrophin microRNAs demonstrate an inverse correlation with dystrophin protein levels. Left panel; The levels of miR-101 were plotted against the calculated % dystrophin of each sample. Linear regression and Pearson's correlation analyses were then performed. The best fit line for each graph is shown in blue and the p-value corresponding to each correlation score is shown in red. Right panel; the relative abundance of miR-101 were plotted according to dystrophin levels of each sample as grouped in Table 1. Statistical analysis was performed in Partek Genomics Suite (One-way ANOVA; $*p<0.05$; $p<0.01$; $*p<0.001$.)

We found an inverse correlation between dystrophin levels and the number of upregulated dystrophin-targeting microRNAs both when we plotted the number of microRNAs versus dystrophin protein amount (FIG. 3a) and when microRNA levels were plotted based upon patient stratification (FIG. 3b) (>1.2 fold change; p<0.05). Using these thresholds, the specific microRNAs was compared between groups, where all microRNAs expressed in BMD patients with high levels of dystrophin (n=4) were also upregulated in BMD moderate and low groups (FIG. 3c-d; Table 2). However, there were many microRNAs expressed in the low level dystrophin biopsies that were not significantly upregulated in the BMD biopsies with high levels of dystrophin. Individual dystrophin-targeting microRNAs were graphed against dystrophin levels in individual biopsies, as well as grouped biopsies (high, medium, low), with many showing statistical significance in terms of correlation coefficients, or groups (FIG. 10; Table 2). As a control, FIG. 11 demonstrates that not all microRNAs show an inverse correlation with dystrophin protein levels. Together, these data strongly suggest that that coordinated expression of dystrophin-targeting microRNAs may contribute to variable dystrophin levels observed in BMD Δ45-47 patients.

Putative Dystrophin-Binding microRNAs are Also Upregulated in DMD, GRMD and mdx

Figure 12:
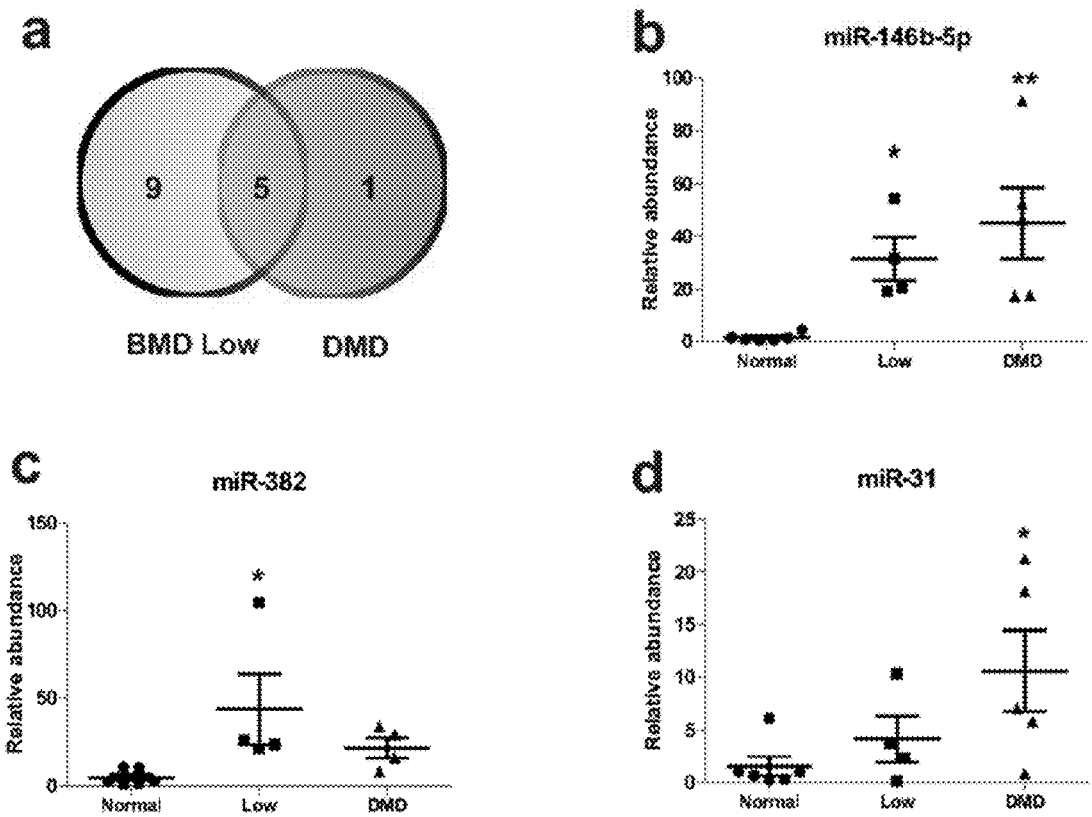
FIG. 12—A subset of dystrophin targeting microRNAs is upregulated both in DMD patients and in BMD patients with low dystrophin levels. (a) Venn Diagram demonstrating the number of upregulated microRNAs detected in BMD low or DMD vs. normal healthy control where the overlap shows those microRNAs that were shared among groups. (b-d) The relative abundance of indicated microRNAs, (b) miR-146b-5p, (c) miR-382, and (d) miR-31 was plotted for Normal, BMD low or DMD patients. Expression values were determined in RQ Manager Software and imported into Partek Genomics Suite 5.0. Statistical analysis was performed in Partek Genomics Suite (One-way ANOVA; $*p<0.05$; $p<0.01$; $*p<0.001$).

MicroRNA profiling microarrays were performed on six DMD patient muscle biopsies, and we found a significant overlap of upregulated microRNAs between the DMD patients and low dystrophin BMD (Table 3, FIG. 12a-d). miR-146b showed the greatest upregulation both in DMD (25-fold) and BMD low (17-fold) muscle biopsies (FIG. 12b). In DMD muscle, miR-31 showed a 6-fold upregulation in microRNA analysis, with a non-statistical upregulation in BMD muscle (p=0.071) (FIG. 12d).

Figures 4A, 4B:
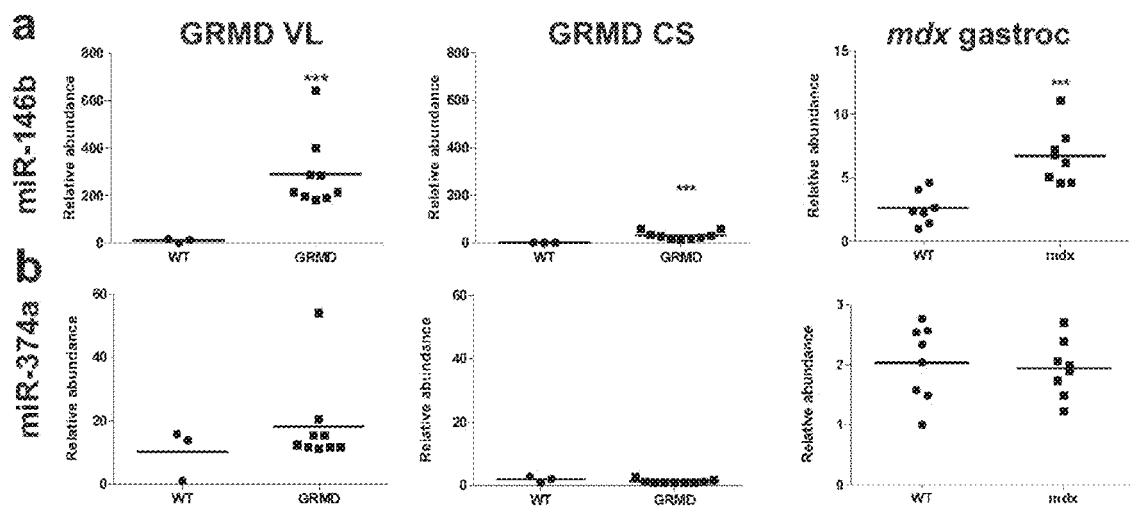
FIG. 4—A subset of dystrophin-targeting microRNAs are upregulated in the GRMD dog and mdx mouse models of DMD and increase as a function of histopathologic severity and age. (a-d) The levels of miR-146b, miR-374a, miR-223, miR-31 and miR-223 were analyzed in WT vs. GRMD dogs in both the more severely affected vastus lateralis (GRMD VL, left panel) and the less severely affected cranial Sartorius (GRMD CS, middle panels) as well as the gastrocnemius of mdx23 mice (mdx gastroc, right panel). Levels of microRNAs were determined using qPCR and are reported as relative abundance by normalization to the lowest WT value. Note the differences of the scales in the Y axis for the VL vs. CS. (e) microRNA levels (miR-146a, miR-146b, miR-223) were assessed in VL muscle biopsies of WT and GRMD dogs of 1 or 2 months of age. All statistical analysis was performed in Prism Graph Pad 5.0 (Student's one-tailed t-test; $*p<0.05$; $*p<0.001$; $**p<0.0001$).
Figures 4C, 4D:
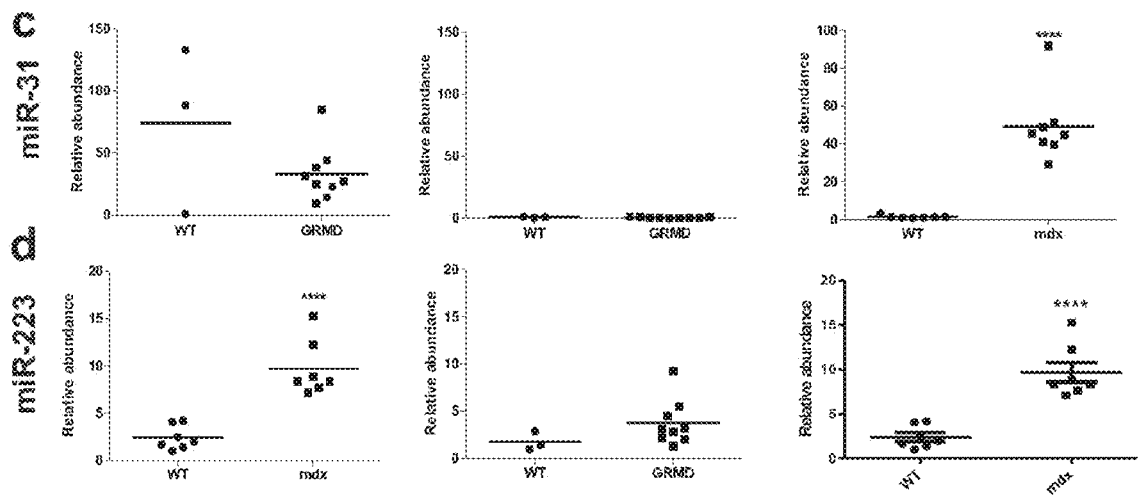
Figure 13:
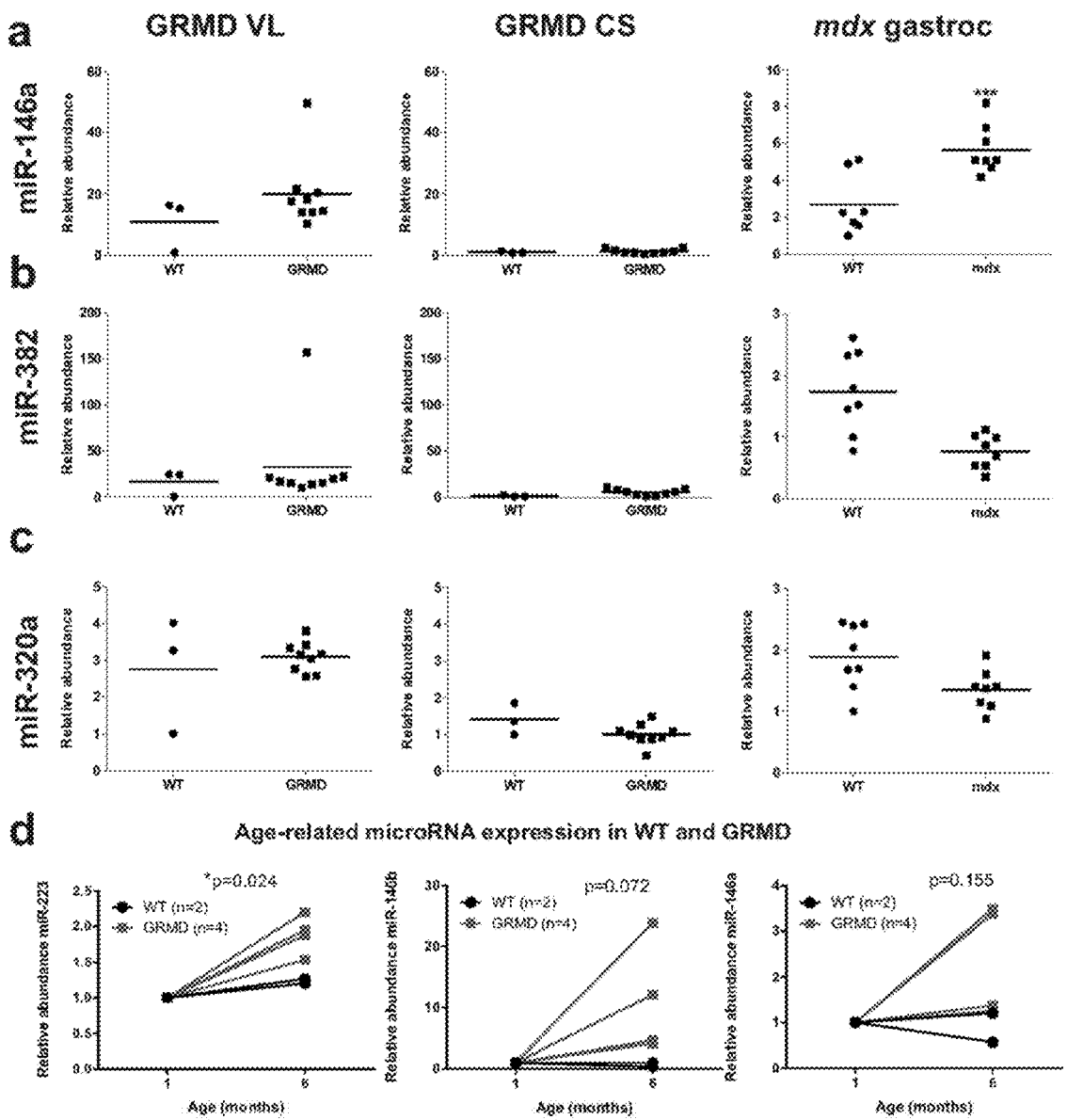
FIG. 13—Expression of dystrophin-targeting microRNAs in the GRMD dog and mdx mouse models of DMD. (a-c) The levels of miR-146a, miR-382 and miR-320a were analyzed in WT vs. GRMD dogs in both the more severely affected vastus lateralus (GRMD VL, left panel) and the less severely affected cranial sartorius (GRMD CS, middle panels) as well as the gastrocnemius of mdx mice (mdx gastroc, right panel). Levels of microRNAs were determined using qPCR and are reported as relative abundance by normalization to the lowest WT value. Note the differences of the scales in the Y axis for the VL vs. CS. All statistical analysis was performed in Prism Graph Pad 5.0 (Student's one-tailed t-test; $**p<0.01$). (d) microRNA levels (miR-223, miR- 146b, miR-146a) from sequential biopsies taken from the right VL at 1 month and the left VL at 6 months in WT and GRMD dogs. Levels were normalized to the "baseline" (1 month) value for each animal and show increases as a function of age. (Student's paired t-test, *p<0.05).

The dog model of DMD (GRMD) shows a severe phenotype similar to human DMD. Different muscle groups show different degrees of pathological involvement, with the vastus lateralis showing age-related severe dystrophic pathology, while the cranial sarotorius is largely spared (Nghiem et al). We found a subset of dystrophin-targeting microRNAs seen in BMD biopsies to be significantly upregulated in the dystrophic dog muscles, however the relative levels varied as a function of age and muscle. As with human BMD and DMD, miR-146b showed the most dramatic elevations, with 500-fold increase in the severely affected vastus lateralis, and 30-fold increase in the mildly affected cranial sartorius (p=0.0002, FIG. 4a). miR-374a (p=0.186, FIG. 4b), and miR-223 (p=0.0107, FIG. 4d), miR-146a (p=0.105, FIG. 13a) were strongly upregulated in the vastus lateralis, but much less so in the sartorius (FIG. 4b, FIG. 13). Three dystrophin-targeting microRNAs upregulated in severe BMD were not significantly changed in the dog muscles (miR-31; FIG. 4c), miR-382 (FIG. 13b), miR-320a (FIG. 13c). The gastrocnemius muscle of mdx mice showed significant upregulation of miR-146b (FIG. 4a), miR-31 (FIG. 4c), miR-223 (FIG. 4d), and miR-146a (FIG. 13a), but not miR-374a (FIG. 4b), miR-382 (FIG. 13b), or miR-320a (FIG. 13c).

Figure 4E:
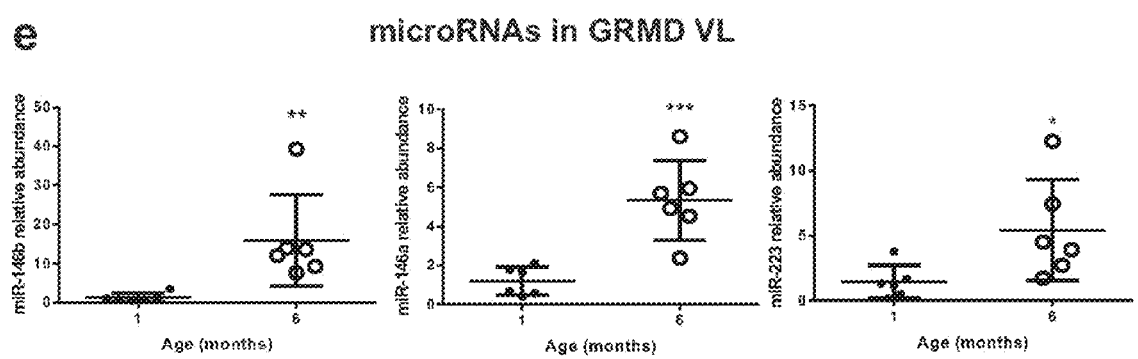

In the GRMD vastus lateralis, we found three microRNAs, miR-146b, miR-146a and miR-223, whose expression significantly increased at from 1 to 2 months (FIG. 4e). Additionally, serial samples from individual dogs taken from the vastus lateralis at 1 and 6 months were analyzed. Within each animal, miR-223 demonstrated a significant increase from 1 to 6 months (p=0.024) and both miR-146b and miR-146a showed non-significant increases with miR-223 reaching statistical significance (p=0.024) (FIG. 13d).

Figure 5:
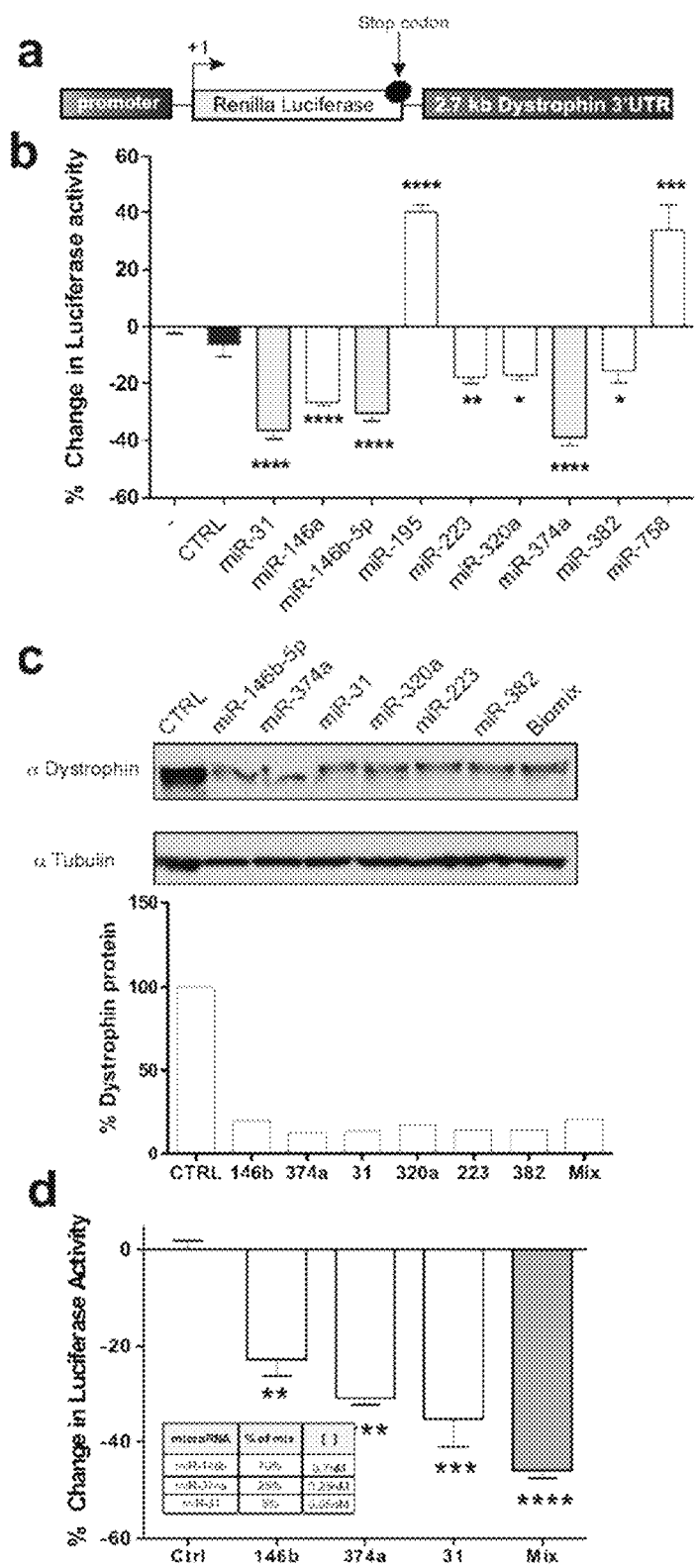
FIG. 5—miR-146b, miR-374a and miR-31 demonstrate potent inhibition of the human dystrophin 3'UTR in vitro. (a) Schematic of the luciferase reporter construct (termed Dys 3'UTR-Luc) used to measure potential inhibition of dystrophin translation by various microRNAs. The psiCheck2 plasmid was obtained from Promega. The entire 2.7 kb dystrophin 3'UTR was cloned downstream of the Renilla luciferase (RLuc) ORF in the pSicheck2 plasmid. (b) Luciferase assay testing the ability of the identified microRNAs to inhibition dystrophin translation in vitro. C2C12 myoblasts were co-transfected with the Dys 3'UTR and 50 uM of indicated microRNA mimics. 48 h. post-transfection renilla luciferase results were read and normalized to an internal control (hLuciferase control by a separate promoter within the same plasmid). Results are reported as percent change relative to untreated. (c) Top; Normal human myoblasts were transfected with 50 nM of the indicated microRNA mimics or a control (CTRL) microRNA mimic. 5 days post-differentiation cells were lysed an analyzed by western blot for dystrophin expression, where tubulin was utilized as a loading control. Bottom; Densitometry of western blot result—band intensities were measured for dystrophin, normalized to tubulin levels and are expressed as percent dystrophin by setting CTRL levels to 100%. (d) Luciferase assay testing the ability of the identified microRNAs or microRNA mix to inhibit dystrophin translation in vitro. C2C12 myoblasts were co-transfected with the Dys 3'UTR and 1 uM of miR-146b, miR-374a, and miR-31 of the indicated Biomix. 48 h. post-transfection renilla luciferase results were read and normalized to an internal control. Results are reported as percent change relative to untreated. Relative quantities of microRNAs the microRNA "Biomix" used for the luciferase experiment shown in the legend. Amounts were calculated based relative quantities of microRNAs from results of the low density microRNA array. Right; All statistical analysis was performed in Prism Graph Pad 5.0, One-Way ANOVA with Bonferroni post-test ($*p<0.05$; $p<0.01$; $*p<0.001$).

Thus, many of the dystrophin-targeting microRNAs seen in human BMD and DMD muscle biopsies were also upregulated in the GRMD dog and mdx mouse muscle. In the dog muscles, there was a correlation with histological and functional involvement of the muscle, where the severely affected vastus lateralis showed considerably more upregulation of dystrophin targeting microRNAs than the mildly affected cranial sartorius. Moreover, the levels of three microRNAs showed marked increases as a function of age.

miR-146b-5p, miR-374a and miR-31 Regulate Dystrophin Protein Production In Vitro To determine if the dystrophin-targeting microRNAs were functional in modulating dystrophin mRNA or protein expression, we cloned the 2.7 kb dystrophin 3'UTR downstream of a luciferase reporter construct (Dys 3'UTR, FIG. 5a). The reporter construct was co-transfected with each of the dystrophin-targeting micoRNA mimics into C2C12 myoblasts. Of the nine dystrophin-targeting microRNAs tested, seven significantly inhibited luciferase protein expression (miR-31, miR-146a, miR-146b-5p, miR-223, miR-320a, miR-374a, and miR-382) (FIG. 5b). Two micro- RNAs significantly enhanced dystrophin protein expression (miR-195, and miR-758, FIG. 5b).

We then validated the ability of a subset to confirm that the indicated microRNAs inhibited endogenous dystrophin protein production; immortalized human myoblasts were transfected with 50 nM scrambled (CTRL) microRNA or 50 nM of the indicated microRNA mimics. 24-hours post transfection cells were switched to differentiation media and allowed to differentiate for 7 days to ensure dystrophin protein expression. Consistent with luciferase results, western blot analysis revealed that all microRNAs reduced dystrophin expression to ~20% of normal levels (FIG. 5c).

We next examined how the combination of the three microRNAs that exhibited the most potent downregulation (miR-146b, miR-31, miR-374a) would affect Dys3'UTR luciferase activity. Based on the relative quantities of microRNAs from the muscle biopsy microRNA analyses, we created a physiologically relevant mixture ('biomix') that consisted of 70% miR-146b, 25% miR-374a, and 5% miR-31 (FIG. 5d). At a sub-optimal dose (1 nM), this microRNA mix exhibited more potent effects than any single microRNA at the same concentration, suggesting that effects were additive or synergistic (FIG. 5s.)

miR-146b-5p, miR-374a and miR-31 Regulate Dystrophin Protein Production In Vivo

Figure 6:
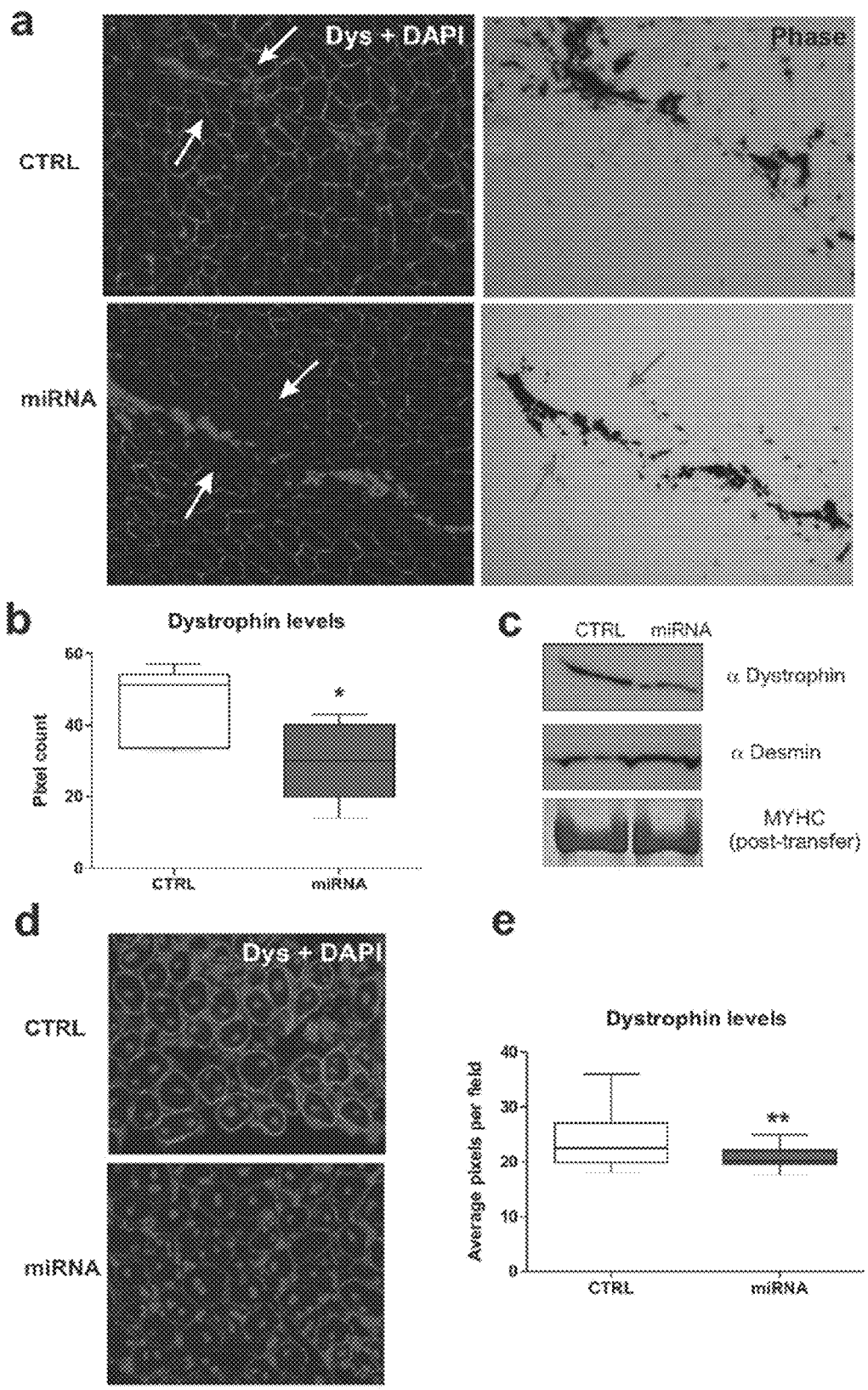
FIG. 6—Physiological mix of miR-146b, miR-374a and miR-31 decreases dystrophin protein levels in vivo. (a-b) The tibialis anterior (TA) of C57BL10/J mice aged 6 weeks mice were injected with 2 ug of the microRNA mix" as listed in FIG. 6d. Muscles were harvested 7 days post-injection and flash frozen in isopentane-cooled liquid nitrogen. (a) Dystrophin protein levels in CTRL and microRNA-injected mice. 8 uM sections were stained for dystrophin and counterstained with 4',6-Diamidino-2-Phenylindole, Dihydrochloride (DAPI). Stained sections were mounted on coverslips an imaged using a Zeiss ApoTome.2 microscope with 10× magnification and every picture was taking using the same threshold for dystrophin staining. Left panels. White arrow indicates injection site; Right panels; Phase where gray arrows indicated tattoo dye used to mark injection site. (b) Average pixel count around injection site of CTRL or microRNA-injected mice. Microscope pictures were analyzed using Image J software. Pictures were set to a threshold of 70 pixels, and then converted to a binary image and total/average pixels were measured. Average pixel count per field is shown in graph. (c-e) 6 week-old C57Bl6 were utilized for experiments. Muscle regeneration was induced by injecting 6 week-old C57BL6 (WT) mice with a bilateral intramuscular injection of 10 ul of 10 μg/ml of notexin per muscle. Three days post-injection, 10 ug of each microRNA mimic was injected into the right TA of mice with a scrambled control mimic (CTRL) was injected into the contralateral (Left) TA. Either 7 days (n=3) or 14 days (n=3) post injection mice were sacrificed and the TA was dissected and flash-frozen in isopentane-cooled liquid nitrogen. (c) Western blot analysis of CTRL or microRNA injected muscle. (d) Dystrophin immunostaining in CTRL and microRNA-injected mice 7 days post-injury. 8 uM sections were stained for dystrophin and counterstained with 4',6-Diamidino-2-Phenylindole, Dihydrochloride (DAPI). Stained sections were mounted on coverslips an imaged using a Zeiss ApoTome.2 microscope with 10× magnification and every picture was taking using the same threshold for dystrophin staining. (e) Average pixel count around injection site of CTRL or microRNA-injected mice. Microscope pictures were analyzed using Image J software. Pictures were set to a threshold of 70 pixels, and then converted to a binary image and total/average pixels were measured. Average pixel count per field is shown in graph. All statistical analyses were performed in Prism Graph Pad 5.0, One-Way ANOVA with Bonferroni post-test ($*p<0.05$; $p<0.01$; $*p<0.001$).
Figure 14:
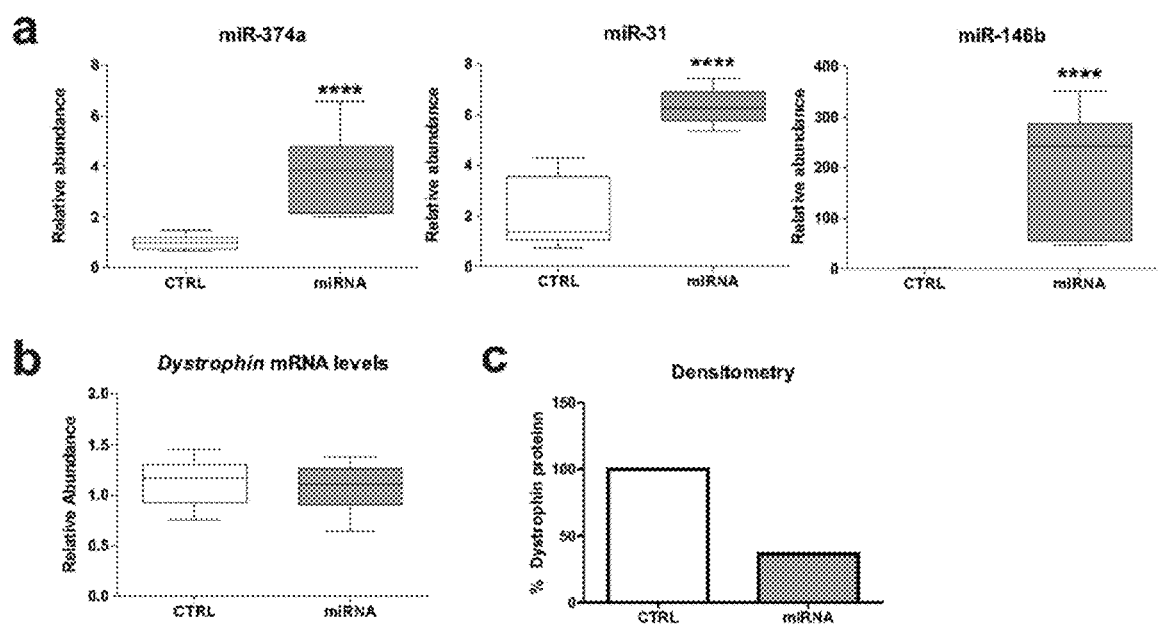
FIG. 14—Physiological mix of miR-146b, miR-374a and miR-31 decreases dystrophin protein levels in vivo. (a) RNA was extracted from sections of harvested muscle. qPCR was then performed to detect the expression levels of miR-146b-5p, miR-374a or miR-31 in control (CTRL) or microRNA-injected (miRNA) mice. (b) qPCR to detect dystrophin transcript levels in CTRL or microRNA injected mice. (c) Densitometry of Western blot analysis from FIG. 7c; band intensities of dystrophin were measured then normalized to MYHC. CTRL-injected mice from day 7 were set to a 100% to determine % dystrophin. All statistical analysis was performed in Prism Graph Pad 5.0, One-Way ANOVA with Bonferroni post-test (*p<0.05; p<0.01; *p<0.001). All statistical analysis was performed in Prism Graph Pad 5.0, Student's one-tailed t test or One-Way ANOVA with Bonferroni post-test (*p<0.05; p<0.01; *p<0.001).

To test the effects of these microRNAs on dystrophin protein expression in vivo, we injected 1.5 µg of the miR-146b/miR-374a/miR-31 mix into the right tibialis anterior (TA) of 6 week old C57BL10/J mice, while the left TA received 1.5 µg of scrambled control mimic (CTRL). Seven days post-injection muscles were harvested and analyzed for microRNA and dystrophin expression. In all injections, tattoo dye was used to precisely mark the injection site, and qPCR used to validate successful intramuscular delivery of the exogenous microRNA (FIG. 14a). Immunofluorescence staining for dystrophin in frozen muscle sections showed a decrease in dystrophin levels of microRNA-injected muscles at the injection site, compared with CTRL scrambled mimics (FIG. 6a, b). While dystrophin protein was reduced in biome-injected muscles, qRT-PCR showed that dystrophin mRNA was not reduced (FIG. 14b), consistent with the data from BMD patients, suggesting translation inhibition as the primary mechanism-of-action of the dystrophin-targeting microRNAs.

Intramuscular injection of modulatory nucleic acids into wild-type muscle shows delivery to only a small region around the injection site (delivery by osmotic shock). To observe a more global reduction of dystrophin driven by exogenous microRNAs, we induced muscle degeneration using notexin prior to delivering microRNA mimics to the TA. This approach also had the effect of removing endogenous dystrophin protein, given the high stability of the dystrophin protein in the intact muscle injections (half-life is approximately 2 months in skeletal muscle) (Wu et al, 2012). The tibialis anterior muscles of 6-week old C57BL6 wild-type mice were injected with 10 µl of 10 µg/µl notexin using a small surgical incision with tattoo dye to mark the exact location of injection. 4 days post-injection mice were injected with 10 µg/µl microRNA mimic using the "biomix" as above or a control mimic. Mice were harvested 7 days post-injury, when dystrophin protein expression typically becomes visible in myotubes by immunostaining (Hoshino et al, 2002). Western blot analysis of the TA demonstrated significant reduction of dystrophin at 7 days post-injury, (FIG. 6c; densitometry, FIG. 14c). Dystrophin immunofluorescence of microRNA vs. CTRL-injected muscles corroborated these results (FIG. 6d-e).

Dystrophin-Regulating microRNAs Modulate Success of Exon Skipping

Figure 7:
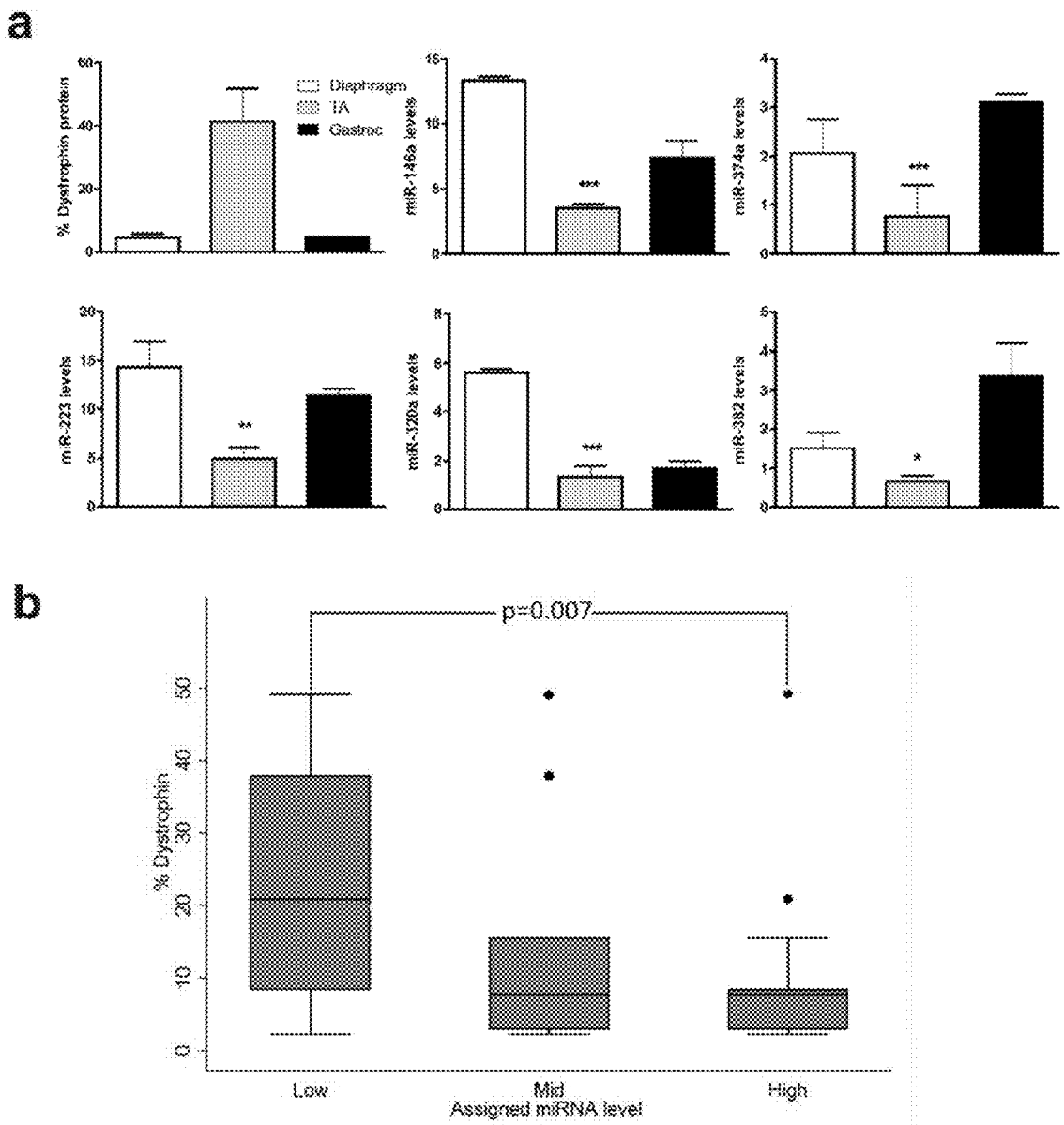
FIG. 7—Dystrophin-regulating microRNAs levels promote observed variability of dystrophin protein production in PMO-treated mdx mice. (a) Dystrophin levels were analyzed via mass spec and miRNA levels were assessed in the diaphragm, TA and Gastroc. Results show an inverse correlation between dystrophin protein levels and dystrophin-regulating microRNA levels. All statistical analyses were performed in Prism Graph Pad 5.0, One-Way ANOVA with Bonferroni post-test ($*p<0.05$; $p<0.01$; $*p<0.001$). (b) The tricep, TA and gastroc in 3 PMO-treated mice were chosen for analysis. Dystrophin levels were analyzed via mass spec and microRNA levels were analyzed via qPCR. For analysis, Each miRNA's values were grouped by muscle, mean and SD were calculated. The deviation from the appropriate mean was calculated for each individual miRNA value. These deviations were assigned a score of low, mid or high, defined by the following rule: those falling within 0.5 SD of the mean were assigned a "mid" score, those greater than 0.5 SD of the mean were assigned a "high score", and those less than 0.5 SD of the mean were assigned a "low" score. Mean % dystrophin levels were then compared using an independent t-test.

We tested whether variable levels of dystrophin-regulating microRNAs in muscle may variability of dystrophin rescue by exon skipping. Mdx23 mice were given a single high dose intravenous injection of 800 mg/kg exon 23-targeting morpholino, and were sacrificed 1 month post-injection with multiple muscle groups dissected (n=3). From one mouse, adjacent cryosections of the tibialis anterior (TA), gastrocnemius, and diaphragm muscles were analyzed for dystrophin protein content by SILAM mass spectrometry (Brown et al. 2013) and immunoblotting, and for dystrophin-regulating microRNA content by TaqMan (real time PCR) assays (FIG. 7a). Dystrophin immunoblot and SILAM mass spectrometry showed concordant dystrophin data, with the TA showing high level rescue by morpholino (40% wild-type levels), and diaphragm and gastrocnemius showing poor rescue (5% wild-type levels) (mass spec data shown FIG. 7a). qPCR of dystrophin-modulating microRNAs (miR-146a, miR-374a, miR-223, miR-320a, miR-382) showed strong correlation with dystrophin protein rescue, where the TA showed low levels of each microRNA and high dystrophin protein, whereas the gastrocnemius and diaphragm showed high levels of microRNAs and low dystrophin rescue (FIG. 7a).

To investigate intra-animal variability in miRNA expression in relation to dystrophin protein levels, two additional morpholino-injected mice with a single high dose injection were studied. Here, different regions of each muscle (non-adjacent cryosections) were studied. These were assayed both for dystrophin protein via mass spec (Brown et al, 2013), and for miRNA levels by qRT-PCR (miR-146a, miR-146b-5p, miR-374a, miR-31, miR-223, miR-382 and miR-320a). Triceps, gastrocnemius and TA of each mouse (n=9 muscles tested; 63 microRNA measures), were grouped into low, mid, or high levels of miRNA expression n each of the 9 muscles tested. miRNA data were then plotted in relation to the percentage of dystrophin rescue relative to wild-type muscle, as determined by quantitative mass spec. Based on this analysis we found that tissues expressing the highest levels of dystrophin had significantly lower microRNA levels than those with low levels of dystrophin (FIG. 7b). Collectively, these data suggest that levels of dystrophin-regulating microRNAs may play a part in both inter and intra-patient variability observed in exon skipping trials.

Glucocorticoids and Next Generation Steroid Therapies

Figure 8:
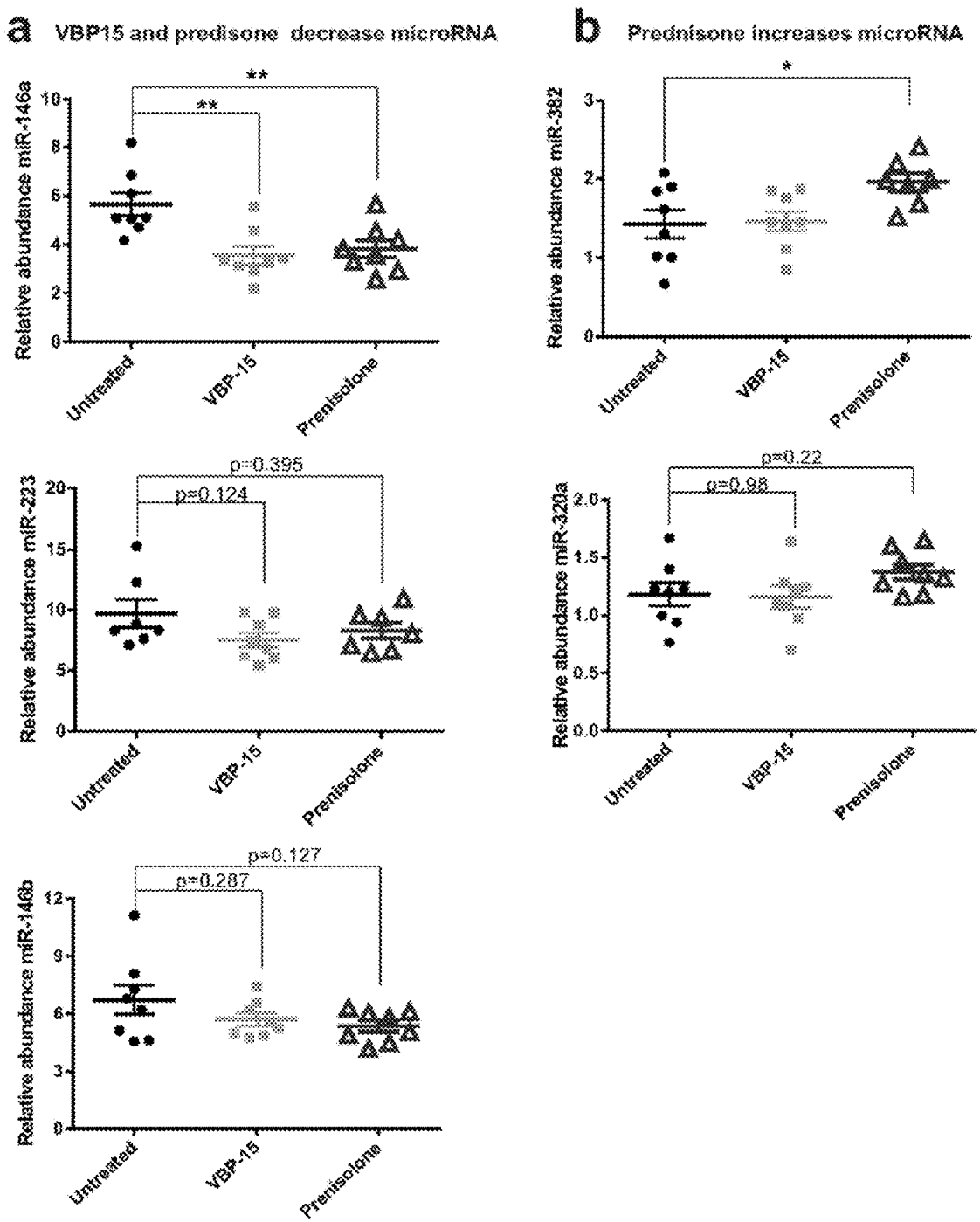
FIG. 8—Treatment with anti-inflammatories modulates dystrophin-targeting microRNAs. (a) VBP15 and prednisolone reduces dystrophin-targeting microRNA levels; miR-146a, miR-146b and miR-223 levels in the gastrocnemius of wild-type mice and vehicle, prednisolone, or control-treated mdx23 mice were assessed via qPCR; results were normalized to wild-type levels. (b) Prednisolone increases dystrophin targeting microRNA levels while VBP15 does not; miR-146a, miR-146b and miR-223 levels were assessed as in (a). All statistical analyses were performed in Prism Graph Pad 5.0, One-Way ANOVA with Bonferroni post-test ($*p<0.05$; $**p<0.01$).

Exon skipping therapies in DMD will likely be used in combination with either current glucocorticoid standards of care, or next-generation steroid derivatives moving towards clinical use (Heier et al 2012). Because these drugs affect transcriptional regulation and/or inflammatory miRNA signaling, we tested what their effects on levels of dystrophin-regulating miRNAs might be. We obtained samples from the gastrocnemius of mdx23 mice treated with 5 mg/kg prednisolone or 15 mg/kg of the novel Δ9,11 compound, VBP-15 (n=8 per group) (Heier et al, 2013). qRT-PCR of dystrophin-modulating microRNAs (miR-146a, miR-374a, miR-223, miR-320a, miR-382) demonstrated that both prednisone and VBP-15 significantly reduced miR-146a levels over untreated mice ($p<0.01$) while miR-146b and miR-223 also showed a trend of decreases (FIG. 8a). Interestingly, miR-382 ($p<0.05$) and miR-320a ($p=0.22$) were increased in prednisone-treated mice, but not in mice treated with the GRE-dissociative VBP15 compound (FIG. 8b). Taken together, these data suggest that glucocorticoids and VBP15 could improve the efficiency of exon skipping therapies at increasing dystrophin by decreasing microRNAs that prevent its translation from the in-frame transcript.

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "dystrophin expression modulator" is used herein to refer to a compound that exhibits an $EC_{50}$ with respect to dystrophin expression activity of no more than about 100 μM and more typically not more than about 50 μM, as measured in the assays described generally herein. "$EC_{50}$" is that concentration of modulator which increases expression of dytrophin to half-maximal level. Certain compounds disclosed herein have been discovered to exhibit modulatory activity against dystrophin expression. In certain embodiments, compounds will exhibit an $EC_{50}$ with respect to dystrophin expression of no more than about 10 μM; in further embodiments, compounds will exhibit an $EC_{50}$ with respect to dystrophin expression of no more than about 5 μM; in yet further embodiments, compounds will exhibit an $EC_{50}$ with respect to dystrophin expression of not more than about 1 μM; in yet further embodiments, compounds will exhibit an $EC_{50}$ with respect to dystrophin expression of not more than about 200 nM, as measured in the assays described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "VBP-15" refers to the following compound:

(10S,13S,16R,17R)-17-hydroxy-17-(2-hydroxyacetyl)-10,13,16-trimethyl-6,7,8,10,12,13,14,15,16, 17-decahydro-3H-cyclopenta[a]phenanthren-3-one

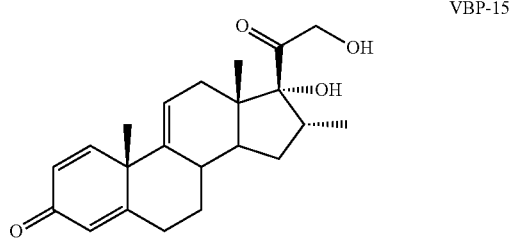 [SMILES: C[C@@H]1CC2C3CCC4=CC(=O)C=C[C@]4(C)C3=CC[C@]2(C)[C@@]1(O)C(=O)CO]

VBP-15

VBP-15, related compounds, and methods of use thereof are disclosed in U.S. Pat. No. 8,207,151, issued Jun. 26, 2012, U.S. patent application Ser. No. 13/639,650, published as US 20130196962 on Aug. 1, 2013, and PCT Patent Application No. PCT/US2012/067003, published as WO 2013082253 on Jun. 6, 2013, each of which are hereby incorporated by reference in their entireties.

The miRNA and protector molecules disclosed herein may be formulated into a composition for storage or for use, for example, in a form and amount suitable for administration to a patient having a dystrophin-mediated disease. While it may be possible for the compounds of the subject invention to be administered as the raw compounds, it is also possible to present them as a pharmaceutical formulation. For example, the compounds disclosed herein may be formulated for administration topically, locally, or systemically in a suitable pharmaceutical carrier such as those described by Remington: The Science and Practice of Pharmacy, 22nd edition (2012), which is hereby incorporated by reference.

Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid. The compounds disclosed herein can be encapsulated by biocompatible microcapsules, microparticles, or microspheres formed of biodegradable or non-biodegradable polymers or proteins, liposomes, or water/oil or oil/water emulsions for targeting to cells.

The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhaler or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.001 to 500 mg/kg per day. The dose range for adult humans is generally from 0.1 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

A composition comprising the miRNA and protector molecules disclosed herein may contain these molecules as fusions or as conjugates with a targeting moiety or with an effector molecule, such as another therapeutic agent. Such analogs may exhibit improved properties such as activity and/or stability. Examples of moieties which may be linked or unlinked to the nucleic acid include, for example, targeting moieties which provide for the delivery of nucleic acid to specific cells, such as to muscle cells, e.g., antibodies to muscle cell antigens.

The miRNA and protector molecules disclosed herein may be administered by means known in the art. Administration of the compositions containing the miRNA or protector molecules disclosed herein may be performed by any acceptable method which allows the protector sequences or nucleic acid encoding the protector sequence to reach its target. These include, but are not limited to, oral, intravenous, intraperitoneal, intrapulmonary, intramuscular, transdermal, subcutaneous, topical, sublingual, or rectal routes. In certain embodiments, the protector molecules disclosed herein will be delivered or targeted directly to muscle tissue capable of expressing dystrophin.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds disclosed herein with stop codon read through antisense exon skipping therapy [drisapersen (exon 51), eteplirsen (exon 51), SRP-4052 (exon 53), SRP-4045 (exon 45), SRP-4050 (exon 50), SRP-4044 (exon 44), SRP-4052 (exon 52), SRP-4055 (exon 55), SRP-4008 (exon 8), PRO044 (exon 44), PRO045 (exon 45), PRO053 (exon 53), PRO052 (exon 52), PRO055 (exon 55)], glucocorticoid receptor modulators, prednisone, prednisolone, VBP-15, and any compounds disclosed in U.S. Pat. No. 8,207,151, issued Jun. 26, 2012 and U.S. patent application Ser. No. 13/639,650, published as US 20130196962 on Aug. 1, 2013.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating dystrophin-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of dystrophin-mediated disorders.

Specific diseases to be treated by the compounds, compositions, and methods disclosed herein include muscular dystrophy, Duchenne muscular dystrophy, Becker muscular dystrophy, limb girdle muscular dystrophy, congenital muscular dystrophy, facioscapulohumeral muscular dystrophy, myotonic muscular dystrophy, oculopharyngeal muscular dystrophy, distal muscular dystrophy, and Emery-Dreifuss muscular dystrophy.

From the foregoing description, one skilled in the art can easily ascertain the essential characteristics of this invention, and without departing from the spirit and scope thereof, can make various changes and modifications of the invention to adapt it to various usages and conditions.

REFERENCES

Each of the following references are hereby incorporated by reference in their entireties.

Anthony K, Arechavala-Gomeza V, Ricotti V, Torelli S, Feng L, Janghra N, Tasca G, Guglieri M, Barresi R, Armaroli A et al (2013) Biochemical Characterization of Patients With In-Frame or Out-of-Frame DMD Deletions Pertinent to Exon 44 or 45 Skipping. JAMA Neurol 71: 32-40.

Anthony K, Arechavala-Gomeza V, Ricotti V, Torelli S, Feng L, Janghra N, Tasca G, Guglieri M, Barresi R, Armaroli A et al (2014) Biochemical Characterization of Patients With In-Frame or Out-of-Frame DMD Deletions Pertinent to Exon 44 or 45 Skipping. JAMA Neurol 71: 32-40.

Anthony K, Cirak S, Torelli S, Tasca G, Feng L, Arechavala-Gomeza V, Armaroli A, Guglieri M, Straathof C S, Verschuuren J J et al (2011) Dystrophin quantification and clinical correlations in Becker muscular dystrophy: implications for clinical trials. Brain 134: 3547-3559.

Beggs A H, Hoffman E P, Snyder J R, Arahata K, Specht L, Shapiro F, Angelini C, Sugita H, Kunkel L M (1991) Exploring the molecular basis for variability among patients with Becker muscular dystrophy: dystrophin gene and protein studies. Am J Hum Genet. 49: 54-67.

Brown K J, Marathi R, Fiorillo A A, Ciccimaro E F, Sharma S, Rowlands D S, Rayavarapu S, Nagaraju K, Hoffman E P, Hathout Y Accurate Quantitation of Dystrophin Protein in Human Skeletal Muscle Using Mass Spectrometry. J Bioanal Biomed Suppl 7.

Brown K J, Marathi R, Fiorillo A A, Ciccimaro E F, Sharma S, Rowlands D S, Rayavarapu S, Nagaraju K, Hoffman E P, Hathout Y (2013) Accurate Quantitation of Dystrophin Protein in Human Skeletal Muscle Using Mass Spectrometry. J Bioanal Biomed Suppl 7.

Cacchiarelli D, Incitti T, Martone J, Cesana M, Cazzella V, Santini T, Sthandier O, Bozzoni I (2011) miR-31 modulates dystrophin expression: new implications for Duchenne muscular dystrophy therapy. EMBO Rep 12: 136-141.

Cacchiarelli D, Martone J, Girardi E, Cesana M, Incitti T, Morlando M, Nicoletti C, Santini T, Sthandier O, Barberi L et al (2010) MicroRNAs involved in molecular circuitries relevant for the Duchenne muscular dystrophy pathogenesis are controlled by the dystrophin/nNOS pathway. Cell Metab 12: 341-351.

Chamberlain J S, Grant S G, Reeves A A, Mullins L J, Stephenson D A, Hoffman E P, Monaco A P, Kunkel L M, Caskey C T, Chapman V M (1987) Regional localization of the murine Duchenne muscular dystrophy gene on the mouse X chromosome. Somat Cell Mol Genet. 13: 671-678.

Chen J F, et al. (2006) The role of microRNA-1 and microRNA-133 in skeletal muscle proliferation and differentiation. Nat Genet. 38(2):228-233.

Cirak S, Arechavala-Gomeza V, Guglieri M, Feng L, Torelli S, Anthony K, Abbs S, Ganalda M E, Bourke J, Wells D J et al (2011) Exon skipping and dystrophin restoration in patients with Duchenne muscular dystrophy after systemic phosphorodiamidate morpholino oligomer treatment: an open-label, phase 2, dose-escalation study. Lancet 378: 595-605.

Eisenberg I, Eran A, Nishino I, Moggio M, Lamperti C, Amato A A, Lidov H G, Kang P B, North K N, Mitrani-Rosenbaum S et al (2007) Distinctive patterns of microRNA expression in primary muscular disorders. Proc Natl Acad Sci USA 104: 17016-17021.

Finkel R S, Flanigan K M, Wong B, Bonnemann C, Sampson J, Sweeney H L, Reha A, Northcutt V J, Elfring G, Barth J et al (2013) Phase 2a study of ataluren-mediated dystrophin production in patients with nonsense mutation duchenne muscular dystrophy. PLoS One 8: e81302.

Greco S, et al. (2009) Common micro-RNA signature in skeletal muscle damage and regeneration induced by Duchenne muscular dystrophy and acute ischemia. Cell Metab 12(4):341-351.

Heier C R, Damsker J M, Yu Q, Dillingham B C, Huynh T, Van der Meulen J H, Sali A, Miller B K, Phadke A, Scheffer L et al (2013) VBP15, a novel anti-inflammatory and membrane-stabilizer, improves muscular dystrophy without side effects. EMBO Mol Med 5: 1569-1585.

Hoffman E P, Bronson A, Levin A A, Takeda S, Yokota T, Baudy A R, Connor E M (2011) Restoring dystrophin expression in duchenne muscular dystrophy muscle progress in exon skipping and stop codon read through. Am J Pathol 179: 12-22.

Hoffman E P, Brown R H, Jr., Kunkel L M (1987a) Dystrophin: the protein product of the Duchenne muscular dystrophy locus. Cell 51: 919-928.

Hoffman E P, Fischbeck K H, Brown R H, Johnson M, Medori R, Loike J D, Harris J B, Waterston R, Brooke M, Specht L et al (1988) Characterization of dystrophin in muscle-biopsy specimens from patients with Duchenne's or Becker's muscular dystrophy. N Engl J Med 318: 1363-1368.

Hoffman E P, Kunkel L M, Angelini C, Clarke A, Johnson M, Harris J B (1989) Improved diagnosis of Becker muscular dystrophy by dystrophin testing. Neurology 39: 1011-1017.

Hoffman E P, Monaco A P, Feener C C, Kunkel L M (1987b) Conservation of the Duchenne muscular dystrophy gene in mice and humans. Science 238: 347-350.

Hoshino S, Ohkoshi N, Ishii A, Shoji S (2002) The expression of dystrophin, alpha-sarcoglycan, and beta-dystroglycan during skeletal muscle regeneration: immunohistochemical and western blot studies. Acta Histochem 104: 139-147.

Huynh T, Uaesoontrachoon K, Quinn J L, Tatem K S, Heier C R, Van Der Meulen J H, Yu Q, Harris M, Nolan C J, Haegeman G et al (2013) Selective modulation through the glucocorticoid receptor ameliorates muscle pathology in mdx mice. J Pathol 231: 223-235.

Kesari A, Pirra L N, Bremadesam L, McIntyre O, Gordon E, Dubrovsky A L, Viswanathan V, Hoffman E P (2008) Integrated DNA, cDNA, and protein studies in Becker muscular dystrophy show high exception to the reading frame rule. Hum Mutat 29: 728-737.

Livak K J, Schmittgen T D (2001) Analysis of relative gene expression data using real-time quantitative PCR and the 2(−Delta Delta C(T)) Method. Methods 25: 402-408.

Lu Q L, Morris G E, Wilton S D, Ly T, Artem'yeva O V, Strong P, Partridge T A (2000) Massive idiosyncratic exon skipping corrects the nonsense mutation in dystrophic mouse muscle and produces functional revertant fibers by clonal expansion. Cell Biol 148: 985-996.

Mamchaoui K, Trollet C, Bigot A, Negroni E, Chaouch S, Wolff A, Kandalla P K, Marie S, Di Santo J, St Guily J L et al (2011) Immortalized pathological human myoblasts: towards a universal tool for the study of neuromuscular disorders. Skelet Muscle 1: 34.

Mendell J, Rodino-Klapac L R, Sahenk Z, Roush K, Bird L, Lowes L P, Alfano L, Gomez A M, Lewis S, Kota J et al (2013) Eteplirsen for the treatment of Duchenne muscular dystrophy. Ann Neurol 74: 637-647.

Naguibneva I, et al. (2006) The microRNA miR-181 targets the homeobox protein HOX-All during mammalian myoblast differentiation. Nat Cell Biol 8(3):278-284.

Nghiem P P, Hoffman E P, Mittal P, Brown K J, Schatzberg S J, Ghimbovschi S, Wang Z, Kornegay J N Sparing of the dystrophin-deficient cranial sartorius muscle is associated with classical and novel hypertrophy pathways in GRMD dogs. Am J Pathol 183: 1411-1424.

Nghiem P P, Hoffman E P, Mittal P, Brown K J, Schatzberg S J, Ghimbovschi S, Wang Z, Kornegay J N (2013) Sparing of the dystrophin-deficient cranial sartorius muscle is associated with classical and novel hypertrophy pathways in GRMD dogs. Am J Pathol 183: 1411-1424.

Roberts T C, et al Expression analysis in multiple muscle groups and serum reveals complexity in the microRNA transcriptome of the mdx mouse with implications for therapy. Mol Ther Nucleic Acids 1:e39.

Schmittgen T D (2001) Real-time quantitative PCR. Methods 25: 383-385.

Spitali P, van den Bergen J C, Verhaart I E, Wokke B, Janson A A, van den Eijnde R, den Dunnen J T, Laros J F, Verschuuren J J, t Hoen P A et al (2013) DMD transcript imbalance determines dystrophin levels. FASEB J 27: 4909-4916.

Sylvius N, et al. MicroRNA expression profiling in patients with lamin A/C-associated muscular dystrophy. FASED J 25(11):3966-3978.

Townsend D, Daly M, Chamberlain J S, Metzger J M (2011) Age-dependent dystrophin loss and genetic reconstitution establish a molecular link between dystrophin and heart performance during aging. Mol Ther 19: 1821-1825.

van den Bergen J C, Wokke B H, Janson A A, van Duinen S G, Hulsker M A, Ginjaar H B, van Deutekom J C, Aartsma-Rus A, Kan H E, Verschuuren J J (2013) Dystrophin levels and clinical severity in Becker muscular dystrophy patients. J Neurol Neurosurg Psychiatry.

van Rooij E, Marshall W S, Olson EN (2008a) Toward microRNA-based therapeutics for heart disease: the sense in antisense. Circ Res 103: 919-928.

van Rooij E, Sutherland L B, Thatcher J E, DiMaio J M, Naseem R H, Marshall W S, Hill J A, Olson E N (2008b) Dysregulation of microRNAs after myocardial infarction reveals a role of miR-29 in cardiac fibrosis. Proc Natl Acad Sci USA 105: 13027-13032.

Vignier N, Amor F, Fogel P, Duvallet A, Poupiot J, Charrier S, Arock M, Montus M, Nelson I, Richard I et al (2013) Distinctive serum miRNA profile in mouse models of striated muscular pathologies. PLoS One 8: e55281.

Wu B, Lu P, Cloer C, Shaban M, Grewal S, Milazi S, Shah S N, Moulton H M, Lu Q L (2012) Long-term rescue of dystrophin expression and improvement in muscle pathology and function in dystrophic mdx mice by peptide-conjugated morpholino. Am Pathol 181: 392-400.

Yokota T, Lu Q L, Partridge T, Kobayashi M, Nakamura A, Takeda S, Hoffman E (2009) Efficacy of systemic morpholino exon-skipping in Duchenne dystrophy dogs. Ann Neurol 65: 667-676.

Yokota T, Nakamura A, Nagata T, Saito T, Kobayashi M, Aoki Y, Echigoya Y, Partridge T, Hoffman E P, Takeda S (2012) Extensive and prolonged restoration of dystrophin expression with vivo-morpholino-mediated multiple exon skipping in dystrophic dogs. Nucleic Acid Ther 22: 306-315.

Zhang X, Azhar G, Wei J Y (2012) The expression of microRNA and microRNA clusters in the aging heart. PLoS One 7: e34688.

What is claimed is:

1. A method for increasing the translation of dystrophin in a patient in need thereof, comprising the administration of a therapeutically active amount of a nucleic acid molecule comprising one or more protector sequences complementary to miR-146a, miR-223, miR-320a, miR374a, and/or miR-382 sequences on the 3'UTR of dystrophin; wherein the 3'UTR seed sequences of dystrophin bound by these miRNAs are selected from the group consisting of:

a. miR-146a:
(SEQ ID NO: 16)
5'-UGAUUGUUCAUAAUACAUAAAGUUCUCUGUAAUUACAACUAAAUUAU-3' DMD b. miR-223:
(SEQ ID NO: 18)
5'-AAGUAUAUAAAUACUAUAGUUAUAUAGAUAAAGAGAU-3' DMD c. miR-320a:
(SEQ ID NO: 19)
5'-CAGGUACUGAGUUCUUACUUGAGUAUCAUAAUAU-3' DMD d. miR-374a Site 1:
(SEQ ID NO: 20)
5'-UUUGUGAAGGGUAGUGGUAUUAUACUGUAGAUU-3' DMD e. miR-374a Site 2:
(SEQ ID NO: 21)
5'-AAUACACAGGACUUAUUAUAUCAGAGU-3' DMD f. miR-374a Site 3:
(SEQ ID NO: 22)
5'-CCAAAUAUAUGCCUUACUAUUGUAUUAUAGUACUGCU-3' DMD;
and g. miR-382:
(SEQ ID NO: 23)
5'-AGCUCCAGAUGUUUCUCAUUUUAAACAACUUUCCACUGACAACGAAA-3' DMD.

2. A method for modulating the expression of dystrophin comprising contacting a cell expressing mRNA encoding dystrophin with the nucleic acid comprising one or more protector sequences complementary to miR-223, miR-320a, miR374a, and/or miR-382 sequences on the 3'UTR of dystrophin; wherein the 3'UTR seed sequences of dystrophin bound by these miRNAs are selected from the group consisting of:

a. miR-223:
(SEQ ID NO: 18)
5'-AAGUAUAUAAAUACUAUAGUUAUAUAGAUAAAGAGAU-3' DMD;

b. miR-320a:
(SEQ ID NO: 19)
5'-CAGGUACUGAGUUCUUACUUGAGUAUCAUAAUAU-3' DMD;

c. miR-374a Site 1:
(SEQ ID NO: 20)
5'-UUUGUGAAGGGUAGUGGUAUUAUACUGUAGAUU-3' DMD;

d. miR-374a Site 2:
(SEQ ID NO: 21)
5'-AAUACACAGGACUUAUUAUAUCAGAGU-3' DMD;

e. miR-374a Site 3:
(SEQ ID NO: 22)
5'-CCAAAUAUAUGCCUUACUAUUGUAUUAUAGUACUGCU-3' DMD;
and f. miR-382:
(SEQ ID NO: 23)
5'-AGCUCCAGAUGUUUCUCAUUUUAAACAACUUUCCACUGACAACGAAA-3' DMD.

3. The method of claim 2, comprising administering the nucleic acid to a subject having muscular dystrophy in an amount effective to increase the expression of dystrophin.

4. The method of claim 3, wherein said muscular dystrophy disease is Becker muscular dystrophy.

5. The method of claim 3, wherein said muscular dystrophy disease is Duchenne muscular dystrophy.

6. The method of claim 3, further comprising the treatment of said patient with a codon read through antisense therapy.

7. The method of claim 3, further comprising the treatment of said patient with an exon skipping antisense therapy.

8. The method of claim 3, further comprising the administration of VBP-15: (10S,13S,16R,17R)-17-hydroxy-17-(2-hydroxyacetyl)-10,13,16-trimethyl-6,7,8,10,12,13,14,15,16,17-decahydro-3H-cyclopenta[a]phenanthren-3-one.

* * * * *